US010335316B2

(12) United States Patent
Bor et al.

(10) Patent No.: US 10,335,316 B2
(45) Date of Patent: Jul. 2, 2019

(54) CAPSULAR MEMBRANE TREATMENTS TO INCREASE ACCOMMODATIVE AMPLITUDE

(71) Applicant: Johnson & Johnson Surgical Vision, Inc., Santa Ana, CA (US)

(72) Inventors: Zsolt Bor, San Clemente, CA (US); Daniel G. Brady, San Juan Capistrano, CA (US); Edward P. Geraghty, Rancho Santa Margarita, CA (US); Carina R. Reisin, Tustin, CA (US); Douglas S. Cali, Mission Viejo, CA (US)

(73) Assignee: Johnson & Johnson Surgical Vision, Inc., Santa Ana, CA (US)

( * ) Notice: Subject to any disclaimer, the term of this patent is extended or adjusted under 35 U.S.C. 154(b) by 0 days.

(21) Appl. No.: 15/671,030

(22) Filed: Aug. 7, 2017

(65) Prior Publication Data

US 2017/0333255 A1    Nov. 23, 2017

Related U.S. Application Data

(60) Continuation of application No. 15/063,135, filed on Mar. 7, 2016, now Pat. No. 9,724,240, which is a
(Continued)

(51) Int. Cl.
*A61F 2/14* (2006.01)
*A61F 9/013* (2006.01)
(Continued)

(52) U.S. Cl.
CPC ............... *A61F 9/013* (2013.01); *A61F 2/16* (2013.01); *A61F 9/00* (2013.01); *A61F 9/007* (2013.01);
(Continued)

(58) Field of Classification Search
CPC ...... A61F 9/013; A61F 9/007; A61F 9/00736; A61F 9/0079; A61F 9/008;
(Continued)

(56) References Cited

U.S. PATENT DOCUMENTS

| 4,134,161 A | 1/1979 | Bayers |
| 4,136,466 A | 1/1979 | Wrue |

(Continued)

FOREIGN PATENT DOCUMENTS

| DE | 102006036800 A1 | 2/2008 |
| EP | 94158 A1 | 11/1983 |

(Continued)

OTHER PUBLICATIONS

Ayaki M., et al., "Histopathologic Study of After-Cataract in the Pseudophakic Rabbit Eye Using in-the-Bag Fixation (II)," Nippon Ganka Gakkai Zasshi, 1990, vol. 94 (6), pp. 559-565—Abstract Only Attached.
(Continued)

*Primary Examiner* — David H Willse
*Assistant Examiner* — Tiffany Shipmon
(74) *Attorney, Agent, or Firm* — Johnson & Johnson Surgical Vision, Inc.

(57) ABSTRACT

This apparatus treats the lens capsule so as to increase accommodation of the eye. The treatment of the lens capsule may comprise treating a portion of the lens capsule so as to stiffen the treated portion and improve accommodation of the eye. The intermediate portion of the lens capsule may be located between an optically used central portion of the lens capsule and a peripheral portion of the lens capsule connected to zonules of the eye. The stiffened intermediate portion of the lens capsule can improve coupling of the peripheral portion of the lens capsule to the central portion of the lens capsule, such that an amount of accommodation
(Continued)

of the optically used central portion of the lens is increased. As the force of the lens capsule to a lens disposed within the lens capsule is increased, the lens may comprise the natural lens of the eye or an artificial lens such as an accommodative IOL. The treatment of the eye to stiffen the intermediate portion may comprise application of one or more of an energy or a substance to the intermediate portion.

9 Claims, 18 Drawing Sheets

Related U.S. Application Data division of application No. 13/043,149, filed on Mar. 8, 2011, now Pat. No. 9,278,026, which is a continuation-in-part of application No. 12/570,780, filed on Sep. 30, 2009, now Pat. No. 8,518,028.

(51) Int. Cl.
*A61F 9/007* (2006.01)
*A61F 9/00* (2006.01)
*A61F 2/16* (2006.01)
*A61F 9/008* (2006.01)

(52) U.S. Cl.
CPC ............ *A61F 9/0008* (2013.01); *A61F 9/008* (2013.01); *A61F 9/0017* (2013.01); *A61F 9/0079* (2013.01); *A61F 9/00736* (2013.01); *A61F 9/00838* (2013.01); *A61F 2009/0087* (2013.01); *A61F 2009/00889* (2013.01); *A61F 2009/00895* (2013.01)

(58) Field of Classification Search
CPC .... A61F 9/00838; A61F 9/00821; A61F 2/16; A61F 2/167; A61F 2/1678; A61F 2/1662; A61F 2009/00872; A61F 2009/00863; A61F 2009/00897
See application file for complete search history.

(56) References Cited

U.S. PATENT DOCUMENTS

| | | | |
|---|---|---|---|
| 4,219,721 A | 8/1980 | Kamen et al. |
| 4,403,354 A | 9/1983 | Rainin |
| 4,435,855 A | 3/1984 | Pannu |
| 4,443,441 A | 4/1984 | Galin |
| 4,463,457 A | 8/1984 | Kelman |
| 4,559,942 A | 12/1985 | Eisenberg |
| 4,575,373 A | 3/1986 | Johnson |
| 4,585,456 A | 4/1986 | Blackmore |
| 4,617,023 A | 10/1986 | Peyman |
| 4,642,113 A | 2/1987 | Dubroff |
| 4,661,109 A | 4/1987 | White |
| 4,662,882 A | 5/1987 | Hoffer |
| 4,666,445 A | 5/1987 | Tillay |
| 4,676,793 A | 6/1987 | Bechert, II |
| 4,681,585 A | 7/1987 | Sayano et al. |
| 4,685,921 A | 8/1987 | Peyman |
| 4,685,922 A | 8/1987 | Peyman |
| 4,687,485 A | 8/1987 | Lim et al. |
| 4,704,016 A | 11/1987 | De Carle |
| 4,764,930 A | 8/1988 | Bille et al. |
| 4,781,718 A | 11/1988 | Lindstrom |
| 4,834,753 A | 5/1989 | Sulc et al. |
| 4,872,876 A | 10/1989 | Smith |
| 4,946,470 A | 8/1990 | Sulc et al. |
| 5,108,429 A | 4/1992 | Wiley |
| 5,147,395 A | 9/1992 | Willis |
| 5,217,491 A | 6/1993 | Vanderbilt |
| 5,225,858 A | 7/1993 | Portney |
| 5,259,813 A | 11/1993 | Abthoff et al. |
| 5,269,813 A | 12/1993 | Yoshida et al. |
| 5,288,293 A | 2/1994 | O'Donnell |
| 5,571,177 A | 11/1996 | Deacon et al. |
| 5,713,892 A | 2/1998 | Shimmick |
| 5,728,156 A | 3/1998 | Gupta et al. |
| 5,984,962 A | 11/1999 | Anello et al. |
| 5,993,438 A | 11/1999 | Juhasz et al. |
| 6,210,005 B1 | 4/2001 | Portney |
| 6,511,508 B1 | 1/2003 | Shahinpoor et al. |
| 6,887,083 B2 | 5/2005 | Umeyama et al. |
| 6,923,955 B2 | 8/2005 | Till et al. |
| 6,976,997 B2 | 12/2005 | Noolandi et al. |
| 7,044,945 B2 | 5/2006 | Sand |
| 2001/0010019 A1 | 7/2001 | Schachar |
| 2002/0103478 A1 | 8/2002 | Gwon et al. |
| 2003/0028248 A1 | 2/2003 | Shahinpoor et al. |
| 2003/0050629 A1* | 3/2003 | Kadziauskas .. A61B 17/320068 606/6 |
| 2003/0139808 A1 | 7/2003 | Shahinpoor et al. |
| 2004/0082993 A1 | 4/2004 | Woods |
| 2004/0111153 A1 | 6/2004 | Woods et al. |
| 2004/0153150 A1 | 8/2004 | Ghazizadeh et al. |
| 2004/0199149 A1* | 10/2004 | Myers ..................... A61F 9/008 606/4 |
| 2004/0243111 A1 | 12/2004 | Bendett et al. |
| 2006/0253196 A1 | 11/2006 | Woods |
| 2006/0265058 A1 | 11/2006 | Silvestrini |
| 2007/0185475 A1 | 8/2007 | Frey et al. |
| 2008/0140192 A1 | 6/2008 | Humayun et al. |
| 2008/0161913 A1 | 7/2008 | Brady et al. |
| 2008/0161914 A1 | 7/2008 | Brady et al. |
| 2010/0292678 A1 | 11/2010 | Frey et al. |

FOREIGN PATENT DOCUMENTS

| | | |
|---|---|---|
| EP | 0278724 A2 | 8/1988 |
| EP | 336318 A2 | 10/1989 |
| EP | 478929 A1 | 4/1992 |
| SU | 1424828 A1 | 9/1988 |
| WO | 8701931 A1 | 4/1987 |
| WO | 9007914 A1 | 7/1990 |
| WO | 9749354 A1 | 12/1997 |
| WO | 0182815 A1 | 11/2001 |
| WO | 02071976 A2 | 9/2002 |
| WO | 03057081 A2 | 7/2003 |
| WO | 2004039295 A1 | 5/2004 |
| WO | 2004039395 A1 | 5/2004 |
| WO | 04082542 A2 | 9/2004 |
| WO | 2007084602 A2 | 7/2007 |
| WO | 2010059847 A1 | 5/2010 |

OTHER PUBLICATIONS

Ayaki M., et al., "Histopathologic Study of After-Cataract in the Pseudophakic Rabbit Eye Using Out-of-the-Bag Fixation," Nippon Ganka Gakkai Zasshi, 1990, vol. 94 (6), pp. 553-558—Abstract Only Attached.

Biedner B., et al., "Subconjunctival Dislocation of Intraocular Lens Implant," American Journal of Opthalmology, 1977, vol. 84 (2), pp. 265-266.

Bloom S.M., et al., "Scleral Fixation Suture for Dislocated Posterior Chamber Intraocular Lens," Ophthalmic Surgery, 1990, vol. 21 (12), pp. 851-854.

Bowman C.B., et al., "Noninvasive Repositioning of a Posterior Chamber Intraocular Lens Following Pupillary Capture," Journal of Cataract and Refractive Surgery, 1991, vol. 17 (6), pp. 843-847.

Chan B.P., et al., "Effects of Photochemical Crosslinking on the Microstructure of Collagen and a Feasibility Study on Controlled Protein Release," Acta Biomaterialia, 2008, vol. 4 (6), pp. 1627-1636.

Chan C.K., "An Improved Technique for Management of Dislocated Posterior Chamber Implants," Ophthalmology, 1992, vol. 99 (1), pp. 51-57.

Corcoran M.F., "Spontaneous Repositioning of a Dislocated Medallion Intraocular Lens," Journal of the American Intra-Ocular Implant Society, 1985, vol. 11 (6), pp. 598-599.

(56) References Cited

OTHER PUBLICATIONS

Flynn H.W., et al., "Management of Subluxated and Posteriorly Dislocated Intraocular Lenses Using Pars Plana Vitrectomy Instrumentation," Journal of Cataract and Refractive Surgery, 1990, vol. 16 (1), pp. 51-56.
Flynn H.W., "Pars Plana Vitrectomy in the Management of Subluxed and Posteriorly Dislocated Intraocular Lenses," Graefe's Archive for Clinical and Experimental Ophthalmology, 1987, vol. 225 (3), pp. 169-172.
Friedberg M.A., et al., "A New Technique for Repositioning and Fixating a Dislocated Intraocular Lens," Archives of Ophthalmology, 1992, vol. 110 (3), pp. 413-415.
Glasser A., "Accommodation" in: Encyclopedia of Eye, vol. 1, Dartt D.A., ed., Oxford Academic Press, 2010, pp. 8-17.
Glasser A., et al., "Accommodation and Presbyopia" in: Adler's Physiology of the Eye, Clinical Application, 10th Edition and 7th Chapter, Kaufman P.L., et al., Eds., Mosby, 2002, pp. 195-233.
Glasser A., "Physiology of Accommodation and Presbyopia" in: Surgery for Hyperopia, Chapter. 2, Sher N.A., Ed., Slack, Inc., 2004, pp. 11-21.
Glasser A., "The Helmholtz Mechanism of Accommodation" in: Hyperopia and Presbyopia, Chapter 3, Tsubota K., et al., eds., Marcel Dekker, Inc., 2003, pp. 27-47.
Henderson B.A., et al., "Stepwise Approach to Establishing an Ophthalmology Wet Laboratory," Journal of Cataract & Refractive Surgery, 2009, vol. 35 (6), pp. 1121-1128.
Hovanesian J.A., et al., "Cataract Wound Closure with a Polymerizing Liquid Hydrogel Ocular Bandage," Journal of Cataract & Refractive Surgery, 2009, vol. 35 (5), pp. 912-917.
Hovanesian J.A., et al., "Watertight Cataract Incision Closure Using Fibrin Tissue Adhesive," Journal of Cataract & Refractive Surgery, 2007, vol. 33 (8), pp. 1461-1463.
International Search Report and Written Opinion for Application No. PCT/US2012/028090, dated Sep. 25, 2012, 19 Pages.
International Search Report and Written Opinion for Application No. PCT/US2012/028095, dated Jun. 19, 2012, 11 pages.
International Search Report and Written Opinion, dated Jan. 14, 2010, and International Preliminary Report on Patentability, dated Mar. 29, 2011, for Application No. PCT/US2009/058321, 11 pages.
International Search Report for Application No. PCT/US2010/050752, dated Mar. 22, 2011, 5 pages.
International Search Report for Application No. PCT/US94/06403, dated Sep. 20, 1994, 4 pages.
Lyons C.J., et al., "Report of a Repositioned Posteriorly Dislocated Intraocular Lens via Pars Plicata Sclerotomy," Journal of Cataract Refractive Surgery, 1990, vol. 16 (4), pp. 509-511.
Menabeuoni L., et al., "Laser-Assisted Corneal Welding in Cataract Surgery: Retrospective Study," Journal of Cataract and Refractive Surgery, 2007, vol. 33 (9), pp. 1608-1612.
Moretsky S.L., "Suture Fixation Technique for Subluxated Posterior Chamber IOL through Stab Wound Incision," Journal of the American Intra-Ocular Implant Society, 1984, vol. 10 (4), pp. 477-480.
Nabors G., et al., "Ciliary Sulcus Suturing of a Posterior Chamber Intraocular Lens," Ophthalmic Surgery, 1990, vol. 21 (4), pp. 263-265.
Neumann A.C., et al., "Complications Associated with STAAR Silicone Implants," Journal of Cataract and Refractive Surgery, 1987, vol. 13 (6), pp. 653-656.
Nevyas H.J., et al., "A YAG Laser Technique to Facilitate Removal of Posterior Chamber Intraocular Lenses from the Capsular Bag," Journal of Cataract and Refractive Surgery, 1987, vol. 13 (2), pp. 201-204.
Pandey S.K., et al., "Creating Cataracts of Varying Hardness to Practice Extracapsular Cataract Extraction and Phacoemulsification," Journal of Cataract & Refractive Surgery, 2000, vol. 26 (3), pp. 322-329.
Pandey S.K., et al., "Induction of Cataracts of Varying Degrees of Hardness in Human Eyes Obtained Postmortem or Cataract Surgeon Training," American Journal of Ophthalmology, 2000, vol. 129 (4), pp. 557-558.
Partial International Search Report for Application No. PCT/US2012/028090, dated May 29, 2012, 6 pages.
Pau H., "Cortical and Subcapsular Cataracts: Significance of Physical Forces," Ophthalmologica, 2006, vol. 220 (1), pp. 1-5.
Poley B.J., et al., "A Closed Technique for Repositioning Dislocated Iris Plane Lenses," Journal of the American Intra-Ocular Implant Society, 1979, vol. 5 (4), pp. 316-320.
Praeger D.L., "Praeger Micro Irrigating Hook Intraocular Lens Implantation," Ophthalmic Surgery, 1979, vol. 10 (7), pp. 30-32.
Ripken T., et al., "Fs-Laser Induced Elasticity Changes to Improve Presbyopic Lens Accommodation," Graefe's Archive for Clinical and Experimental Ophthalmology, 2008, vol. 246 (6), pp. 897-906.
Shentu X., et al., "Combined Microwave Energy and Fixative Agent for Cataract Induction in Pig Eyes," Journal of Cataract & Refractive Surgery, 2009, vol. 35 (7), pp. 1150-1155.
Smiddy W.E., "Dislocated Posterior Chamber Intraocular Lens: A New Technique of Management," Archives of Ophthalmology, 1989, vol. 107 (11), pp. 1678-1680.
Smiddy W.E., et al., "Management of Dislocated Posterior Chamber Intraocular Lenses," Ophthalmology, 1991, vol. 38 (6), pp. 889-894.
Stark W.J., et al., "Management of Posteriorally Dislocated Intraocular Lenses," Ophthalmic Surgery, 1980, vol. 11 (8), pp. 495-497.
Sternberg P., et al., "Treatment of Dislocated Posterior Chamber Intraocular Lenses," Archives of Ophthalmology, 1986, vol. 104 (9), pp. 1391-1393.
Sugiura T., et al., "Creating Cataract in a Pig Eye," Journal of Cataract & Refractive Surgery, 1999, vol. 25 (5), pp. 515-621.
Tseng Y., et al., "How Actin Crosslinking and Bundling Proteins Cooperate to Generate an Enhanced Cell Mechanical Response," Biochemical and Biophysical Research Communications, 2005, vol. 334 (1), pp. 183-192.
Wand M., et al., "Thymoxamine Hydrochloride:An Alpha-adrenergic Blocker," Survey of Ophthalmology, 1980, vol. 25(2), pp. 75-84.
Weeber H.A., et al., "The Role of the Capsular Bag in Accommodation" in: Current Aspects of Human Accommodation II, Guthoff R., eds., Heidelberg, Kaden Verlag, 2003, pp. 119-126.

\* cited by examiner

CAPSULAR MEMBRANE TREATMENTS TO INCREASE ACCOMMODATIVE AMPLITUDE

This application is a continuation of and claims priority to U.S. application Ser. No. 15/063,135, filed Mar. 7, 2016, which is a divisional application of and claims priority to U.S. application Ser. No. 13/043,149, filed on Mar. 8, 2011, issued as U.S. Pat. No. 9,278,026, which is a continuation-in-part of and claims priority to U.S. application Ser. No. 12/570,780, filed on Sep. 30, 2009, issued as U.S. Pat. No. 8,518,028, which are hereby incorporated by reference in their entirety for all purposes as if fully set forth herein.

BACKGROUND OF THE INVENTION

The present invention relates to accommodation of the eye and treatment of presbyopia.

The eye has a cornea and a lens. The cornea and lens focus light on a retina such that the person can perceive the image with the retina located on the back of the eye. When the image on the retina is focused, the image appears sharp to the patient. However, when the image is out of focus, the image appears blurred. An eyeglass prescription to correct far vision of the eye can be referred to clinically as a refraction of the eye, and the measured refraction of the eye can include a sphere, a cylinder and an axis of the cylinder. Corrective lenses can be prescribed based on the refraction of the eye such that optical errors of the eye such as nearsightedness, also referred to as myopia, and farsightedness, also referred to as hyperopia, can be corrected. Nearsightedness corresponds to an eye having too much optical power such that objects near the eye appear in focus and distant objects appear blurred. With a nearsighted eye, lenses having negative optical power can be used to correct the refractive error of the eye. Farsightedness can refer to an eye not having enough optical power such that positive lenses placed in front of the farsighted eye can correct near vision.

In the normal healthy eye, the lens of the eye can accommodate to both near and far distances of the object viewed such that the image of the object is focused on the retina and remains sharp to the patient. For far vision, the ciliary muscles of the eye can relax and adjust the lens to focus on a far object that may be several meters away. For near vision, the ciliary muscles of the eye can constrict and adjust the lens to focus on a near object. The near object can be located at a distance suitable for reading, for example. The eye can accommodate with movement of the lens to focus on objects at intermediate distances.

With age the accommodation of the eye can decrease such that a person with good distance vision may benefit from lenses to see near objects clearly. The decrease of accommodation of the eye corresponding to presbyopia may be related to a stiffer crystalline lens that decreases the accommodative amplitude of the lens of the eye in at least some instances. People who are near sighted and wear glasses for distance vision may find glasses that correct sight for far vision do not provide near vision correction in at least some instance. This loss of accommodation of the eye can be referred to as presbyopia.

Although many forms of optical correction and devices have been proposed to treat presbyopia, at least some of these approaches have one or more deficiencies such that the prior correction of presbyopia may be less than ideal in at least some instances. Although reading glasses can be effective when worn, in at least some instances a person may not have glasses and need near vision. Also, switching from near vision to far vision with reading glasses can be less than ideal in at least some instances. Although bifocals are available, such corrective lenses may provide less than ideal results in at least some instances such as when a person engages in water sport or sweats such that the correction of the lenses can be at least partially distorted.

Although it has been proposed to reduce the stiffness of the natural crystalline lens through laser treatment allowing for improvement in the ability of the crystalline lens to change power, in at least some instances it is possible to create a premature cataract. Also, treatments of the lens can potentially result in changes in refraction that may require the patient to wear glasses in at least some instances. Further, at least some tissue treatments can be unstable in at least some instances such that the treatment results in no more than a temporary change to the eye in at least some instances. For example, electrocautery of the lens capsule may result in decreased thickness of the lens capsule that may contribute to cataract formation and may be related to unstable refraction of the eye in at least some instances.

Patients who receive intraocular lenses (hereinafter "IOLs") may have no effective accommodation, and may be considered presbyopic in at least some instances. For example, although IOL surgery to replace a cataract of the natural lens of the eye can be effective in restoring vision of the patient, such patients cannot accommodate effectively in at least some instances.

Although multifocal lenses have been proposed, such lenses can result in undesirable visual phenomenon (hereinafter "dysphotopsia") in at least some instances. Although multifocal lens may provide a first optical correction for near vision and a second optical power for distance vision, the light rays having the second optical power for near vision may provide visual phenomenon such as halos for a distant object, for example when the patient views a distant object.

One promising approach to treat patients who have received IOLs for cataract surgery has been to introduce an accommodating IOL. However, such IOLs have resulted in less accommodation than would be ideal and can be more difficult to implant in at least some instances. Also, recovery time of accommodating IOLs may be longer than a non-accommodating IOL, in at least some instances. Also, the accommodative abilities may not be restored as would be ideal in at least some instances. Though vision may be improved, the degree of improvement can vary among patients and may be less predictable than would be ideal in at least some instances.

In light of the above, it would be desirable to provide improved methods and apparatus for treating vision that overcome one or more of the above mentioned limitations of the prior approaches. Ideally such methods and apparatus would restore accommodation to provide near and far vision correction with reduced side effects.

SUMMARY OF THE INVENTION

Embodiments of the present invention provide treatment of the lens capsule so as to increase accommodation of the eye. The treatment of the lens capsule may comprise treating an intermediate portion of the lens capsule so as to stiffen the treated intermediate portion and improve accommodation of the eye. The intermediate portion of the lens capsule may be located between an optically used central portion of the lens capsule and an elastic peripheral portion of the lens capsule connected to zonules of the eye. The intermediate portion of the lens capsule may comprise an intermediate portion of the anterior lens capsule, or an intermediate portion of the posterior lens capsule, or combinations thereof. The stiffened intermediate portion of the lens capsule can improve coupling of the elastic peripheral portion of the lens capsule to the central portion of the lens capsule or an IOL at least partially within the capsule, such that an amount of accommodation of the optically used central portion of the natural lens or IOL can be increased. The accommodation of the eye can be increased based on an increased curvature of the optically used central portion of the natural lens or IOL, or based on an increased anterior axial movement of the optically used central portion of the natural lens or IOL, or combinations thereof, when the eye accommodates. In many embodiments, the thickness of the treated intermediate portion is maintained substantially, such that the treated intermediate portion substantially resists and decreases radial movement so as to improve coupling and increase radial forces of the peripheral portion of the lens capsule. The stiffened intermediate portion may comprise an annular shape profile such as a ring or annular oval extending substantially continuously around the central portion so as to enclose the central portion, such that radial motion and stretching of the intermediate portion can be decreased substantially. The stiffened intermediate portion comprising the annular shape profile can decrease circumferential stretching of the intermediate portion that may correspond to the radial movement of the intermediate portion, so as to decrease radial movement of the intermediate portion corresponding to the circumferential stretching of the intermediate portion.

The increased amount of accommodation may comprise one or more of an increased radially inward force from the peripheral portion of the lens capsule toward the central portion of the lens capsule, increased anterior movement of the anterior lens capsule, increased movement of the lens anteriorly, increased curvature of the lens, an increased curvature of the central portion of the anterior lens capsule, or a protrusion of the central portion of the anterior lens capsule having the increased curvature, or combinations thereof. As the radially inward force from the lens capsule to a lens disposed at least partially within the lens capsule can be increased, the lens may comprise the natural lens of the eye or an artificial lens such as an accommodating IOL. When used to increase accommodation of the natural lens of the eye, the treatment can be applied to an anterior surface of the anterior lens capsule so as to decrease invasiveness of the procedure and inhibit cataract formation. The treatment of the eye to stiffen the intermediate portion may comprise an agent to stiffen the intermediate portion such as one or more of an energy, a substance to the applied to the intermediate portion, or a support coupled to the intermediate portion. The energy may comprise one or more of electromagnetic energy, RF energy, microwave energy, light energy, UV light energy, visible light energy or infrared light energy to stiffen the portion. The agent may comprise a substance applied to the portion so as to stiffen the portion, for example a stiffening adhesive, a tissue adhesive, or a tissue fixative, or for example riboflavin, or a substance to inhibit nutrients to the portion. The amount of treatment may comprise enough energy or substance so as to stiffen the intermediate portion of the lens capsule without substantially shrinking the intermediate portion, such that far vision of the eye is substantially maintained. The stiffening treatment may be combined with an additional treatment, such as a softening treatment, so as to soften tissue of the lens capsule disposed between the central portion and the stiffened intermediate portion so as to increase accommodation of the central portion.

In a first aspect, embodiments of the present invention provide a method of treating an eye having a lens capsule and a lens, such as a natural lens or an IOL. The lens capsule has a central portion, a peripheral portion and an intermediate portion. The peripheral portion is connected to zonules of the eye. The intermediate portion corresponds to a location between the peripheral portion and the central portion. The intermediate portion of the lens capsule is treated so as to stiffen the intermediate portion of the capsule and increase curvature or movement of at least a portion of the lens when the eye accommodates. The increased curvature can be combined with the increased movement to increase an amount of accommodation of the eye.

The increased curvature of the lens may comprise an increased curvature of a natural lens of the eye or an increased curvature of an IOL, and the increased movement anteriorly may comprise an increased axial movement of the natural lens of the eye or an increased axial movement of the IOL implanted in the eye.

In many embodiments, the increased curvature of the lens may comprise an increased curvature of natural lens of the eye or an increased curvature of an IOL, and the increased movement anteriorly may comprise an increased movement of the natural lens of the eye or an increased movement of the IOL implanted in the eye.

In many embodiments, the intermediate portion is stiffened without shrinking substantially tissue of the intermediate portion such that far vision of the eye is maintained. The intermediate portion can be stiffened such that far vision of the eye is maintained to within about 1D and the accommodation is increased by at least about 1D. In many embodiments, the far vision refraction of the eye is maintained to within about 0.5 D, and the accommodation is increased by about 1D. The intermediate portion of the capsule may be treated so as to maintain the optical clarity and corresponding image quality of the intermediate portion when the intermediate portion is stiffened. Alternatively or in combination, the intermediate portion of the capsule may be treated so as to maintain substantially the thickness and corresponding distance vision of the intermediate portion of the lens capsule when stiffened.

In many embodiments, the capsule comprises an anterior capsule and the intermediate portion comprises an intermediate portion of the anterior capsule. The lens may comprise the natural lens of the eye, and the treatment can be applied to the intermediate portion of the anterior capsule without penetration of the capsule.

In many embodiments, the central portion of the capsule is coupled to the peripheral portion of the capsule with the stiffened intermediate portion such that the central portion is moved forward when the eye accommodates and peripheral portion moves inward. The central portion of the lens capsule may move anteriorly along an axis of the eye a first amount and the intermediate portion may move anteriorly along the axis a second amount, in which the first amount is greater than the second amount such that the curvature of the central portion is increased when the eye accommodates.

In many embodiments, the capsule comprises a posterior capsule and the intermediate portion comprises an intermediate portion of the posterior capsule.

In many embodiments, treating the intermediate portion comprises delivering one or more of an energy or a substance to the intermediate portion. The energy may comprise one or more of thermal energy, mechanical energy, or electromagnetic energy. The electromagnetic energy may comprise RF energy, microwave energy, light energy, UV light energy, visible light energy or infrared light energy. The substance may comprises one or more of an adhesive, a thermoreversible adhesive, a setae based adhesive, a curable adhesive, a tissue fixative, a crosslinker, a photo-sensitive crosslinker, or a substance to inhibit nutrients to the intermediate portion. The substance can be suitable for a chemical reaction, such as a photochemical reaction, and may comprise cross-linker, such as a photosensitive cross-linker.

In many embodiments, the light energy is transmitted through the cornea of the eye and absorbed with the intermediate portion to treat the intermediate portion.

In many embodiments, the one or more of the energy or the substance is delivered to the intermediate portion of the capsule with a probe tip and the probe tip is introduced into an anterior chamber of the eye through an incision in an outer portion of a cornea.

In many embodiments, the substance comprises one or more of an adhesive, a thermoreversible adhesive, a setae based adhesive, a curable adhesive, a tissue fixative, riboflavin, or a substance to inhibit nutrients to the intermediate portion.

In many embodiments, the one or more of the energy or the substance is delivered to the intermediate portion of the capsule with a probe tip and the probe tip is introduced into an anterior chamber of the eye through an incision in an outer portion of a cornea.

In many embodiments, a capsulorhexis is performed to remove the central portion of the capsule and place an intraocular lens within the capsule.

In many embodiments, the stiffened intermediate portion decreases radial movement of the capsulorhexis edge such that radially inward force of the peripheral portion is increased by at least about 1 g when the eye accommodates.

The intermediate portion of the capsule can be treated before performing the capsulorhexis to remove the central portion of the capsule, and at least a portion of the stiffened intermediate portion of the capsule remains so as to move the peripheral portion inward when the eye accommodates with the intraocular lens.

In many embodiments, the stiffened portion supports the peripheral portion such that the peripheral portion moves the intraocular lens forward with a force of at least about 3 g.

In many embodiments, the lens capsule is retreated with a second treatment to stiffen the lens capsule at least about one day after the treatment to increase the amount of accommodation of the eye.

In many embodiments, the lens with is treated a softening treatment located inward of the treatment to stiffen the intermediate portion capsule so as to couple the stiffened intermediate portion to the softened tissue to increase the amount of accommodation of the eye.

In another aspect, embodiments of the present invention provide and apparatus to treat an eye. The eye has a lens comprising a capsule. The apparatus comprises a delivery device to couple to an intermediate portion the capsule to deliver one or more of an energy or a substance to the intermediate portion. Circuitry is coupled to the delivery device to deliver the one or more of the energy or the substance to the eye to stiffen the intermediate portion.

In many embodiments, the circuitry is configured to deliver the one or more of the energy or the substance to the intermediate tissue with a treatment profile so as to stiffen the tissue without shrinking substantially tissue of the intermediate portion.

In many embodiments, the circuitry comprises a processor having computer readable memory, the computer readable memory having instructions stored thereon to treat the tissue with the treatment profile.

In another aspect, embodiments provide an apparatus to treat an eye, in which the eye has a lens and a lens capsule. The lens capsule has an intermediate portion extending between a central portion of the lens capsule and a peripheral portion of the lens capsule. The apparatus comprises a deflectable structure to couple to the intermediate portion the lens capsule to deliver an agent to the intermediate portion so as to stiffen the intermediate portion, and the deflectable structure comprises an amount of the agent sufficient to stiffen the intermediate portion.

In many embodiments, the deflectable structure is sized to pass through an incision of no more than about 2 mm, and the deflectable structure comprise a first configuration to provide a narrow profile for insertion through the incision and a second configuration to provide a wide profile for placement on the intermediate portion of the capsule. The first configuration may comprise one or more of a folded or rotated configuration for passage through the incision and the second configuration may comprise one or more of an unfolded or a c-shaped configuration for placement on the intermediate portion of the capsule.

In another aspect, embodiments provide a method of treating an eye having a lens and a lens capsule. The capsule has a central portion and a peripheral portion connected to zonules of the eye. An adhesive is applied to the intermediate portion of the capsule to stiffen the intermediate portion to increase one or more of curvature or movement of the lens when the eye accommodates. The intermediate portion is located between the central portion and the peripheral portion.

BRIEF DESCRIPTION OF THE DRAWINGS

FIG. 2A-1 shows a stiffness profile of the lens capsule, in accordance with embodiments;

FIG. 2A-2 shows a protrusion and increased curvature of the anterior lens capsule when the eye accommodates with intermediate portion of the lens capsule stiffened to increase accommodation, in accordance with embodiments of the present invention;

FIG. 2A-3 shows the elevation, diameter and increased optical power of the protrusion as in FIG. 2A-2 when the eye accommodates;

FIG. 2A-4 shows the optical power of the central portion of the lens corresponding to the protrusion of the central portion of the lens capsule when the eye accommodates, in accordance with embodiments of the present invention;

FIGS. 5B1 and 5B2 show the structure comprising an expanded wide profile configuration, and narrow profile configuration for insertion into the eye through an incision in the cornea, respectively, in accordance with embodiments;

FIG. 5B3 shows a narrow profile configuration for insertion into the eye through the incision with rotation of the structure as shown in FIG. 5B1;

DETAILED DESCRIPTION OF THE INVENTION

Embodiments of the present invention as described herein can be used in many ways to improve accommodation of the presbyopic eye such that accommodation is increased to at least some extent. The embodiments as described herein can be used to treat presbyopia with an otherwise healthy eye, in a non-invasive or minimally invasive manner, such that the accommodation of the natural lens of the eye is enhanced. The embodiments as described herein can also be used in conjunction with IOLs such that the amount of accommodation with the IOL can be increased. The treatment of the capsular tissue can increase radially inward force to an IOL from about 1 gram (hereinafter "g") to at least about 3 g, for example at least about 4 g, in exemplary embodiments at least about 6 g, so as to provide corresponding improvement in accommodation, for example at least about a two fold increase, for example about a three fold increase, in the amount of accommodation when combined with a commercially available accommodating IOL.

The embodiments as described herein can be used in combination with enhancements to the crystalline lens or with the cornea, or with a phakic IOL or intracorneal inlays, for example. The treatment may comprise treatment of the capsule such that the other portions of the lens remain substantially untreated. Alternatively, the crystalline lens may be softened with a laser in conjunction with treating the capsule. Embodiments as described herein can also be used with accommodating IOLs so as to increase substantially the amount accommodation of the implanted accommodating IOLs. The accommodating IOL may comprise a deformable IOL that can provide increased curvature when the eye accommodates, or an IOL in which the treatment increases axial movement of the substantially rigid lens when the eye accommodates, or combinations thereof. For example the treatment can be combined with an IOL having a substantially rigid lens in which the treatment increases axial movement of the lens.

The stiffening of the capsule to increase the amount of accommodation can be done in many ways. Stiffening of the capsule can be done to increase the power change by creating stiffening rings and/or regions that can amplify the optical power change, for example by increasing curvature of the lens capsule. The capsule can be stiffened with use of methods such as laser, mechanical, electrical (radiofrequency) or chemical.

Alternatively or in combination with increasing an amount of accommodation of the eye, the stiffening treatment as described herein can be used to treat astigmatism of the eye, and may decrease spherical aberration of the eye, for example with increased accommodation of the eye.

As used herein, stiffness encompasses a relationship between stress and strain. The relationship can be linear, or non-linear, or combinations thereof, for example.

Figure 1A:
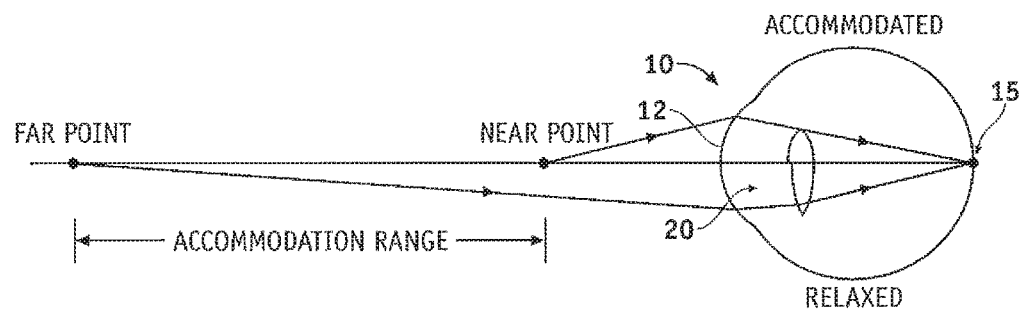
FIG. 1A shows accommodation of an eye, suitable for incorporation in accordance with embodiments of the present invention.

FIG. 1A shows accommodation of an eye 10. The eye 10 has a cornea 12 and a lens 20. The cornea and lens focus light on a retina 15 such that the patient perceives the image with the light sensitive tissue of the retina. When the image on the retina is focused, the image appears sharp to the patient. However, when the image is out of focus, the image appears blurred. The lens 20 of the eye accommodates to the distance of the object viewed such that the image of the object is focused on the retina and remains sharp to the patient. For far vision, the lens 20 of eye 10 relaxes to focus on a far point. The far point can be several meters away, such that the vergence of the target is approximately 0 Diopters. The near point can be located at a distance suitable for reading, for example, and can be about 12 inches (⅓ meter) from the eye, for example, such that the vergence of the object is about 3 Diopters. The accommodation range corresponds to the range over which the eye can accommodate so as to bring the viewed object into focus. The amount of accommodation can be expressed with the optical power used to bring an object into focus, and the optical power can be expressed in units of Diopters (hereinafter "D), to bring the object into focus. For an emmetropic eye capable of focusing on an object at a far distance of about 10 meters and an object at a near distance of about ⅓ of a meter from the patient, the amount of accommodation expressed as a range of optical power is at least about 3D.

Figure 1B:
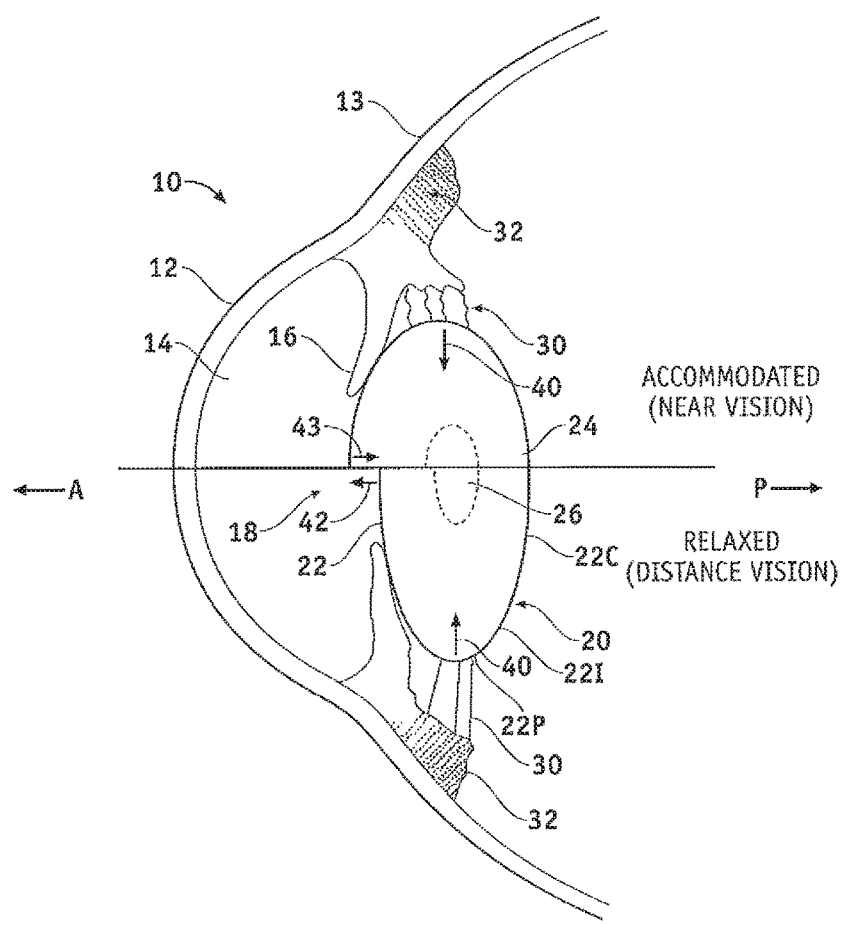
FIG. 1B shows structures of the eye as in FIG. 1A.

FIG. 1B shows structures of the eye as in FIG. 1A. The eye 10 comprises cornea 12, an anterior chamber 14 and an iris 16. The cornea 12 has about two thirds of the optical power of the eye, and is optically coupled to the lens 20 so as to focus light on the retina of the eye. The eye 10 has a sclera 13 comprising the visible white portion of the eye. The iris 16 can define a pupil 18 of the eye. The eye may comprise a visual axis or optical axis 11, for example a line of sight corresponding to a center of the pupil. The iris 16 may contract slightly when the eye accommodates. The lens 20 comprises a capsule 22, a cortex 24 and a nucleus 26. The eye has ciliary muscles 32 connected to ciliary zonules 30. The ciliary zonules 30 are connected to lens capsule 22 at a peripheral portion 22P of the lens capsule.

Description of the eye 10 suitable for combination in accordance with the embodiments as described herein with reference to FIG. 1A and FIG. 1B is at least partially described in one or more the following publications by Adrian Glasser:

Glasser, A. (2010) Accommodation. In: Darlene A. Dartt, editor. Encyclopedia of Eye, Vol I. Oxford: Academic Press; p. 8-17.
Glasser, A. (2004) Physiology of Accommodation and Presbyopia, In *Surgery for Hyperopia*. Ed. Neil Sher, pp. 11-21, SLACK, Inc. Thorofare, N.J.
Glasser, A. (2003) The Helmholtz Mechanism of Accommodation. In *Current Research in Eye Surgery Technology* (CREST). Eds. K. Tsubota, B. S. Boxer Wachler, D. T.
Azar, D. Koch. pp. 27-47. Marcel Dekker, Inc., NewYork.
Glasser, A. and Kaufman, P, L. (2002) Accommodation and Presbyopia. In *Adler's Physiology of the Eye*. 10th Edition. Eds Kaufman P. L. and Alm, A. pp. 195-233.
Mosby, SI. Louis.

During accommodation, the lens and ciliary components of the eye adjust to bring an object into focus. When the eye has a "relaxed" configuration for far vision, the ciliary muscle 32 of the eye is relaxed such that zonules 30 pull the lens capsule 22 outward. When the eye accommodates for near vision, the ciliary muscle 32 contracts such that zonules 30 allow the lens peripheral portion 22P of the lens capsule to move radially inward with a radially inward force 40. When the peripheral portion 22P moves radially inward, the front portion of the lens capsule moves forward with anterior movement 42 such that the anterior optical surface of the lens moves forward so as to bring the image of the near object into focus on the retina. In addition, the curvature of the anterior surface of the lens 20 can increase when the front portion of the lens capsule moves forward so as to increase the optical power of the lens 20 and bring the image of the object into focus on the retina. When the peripheral portion 22P moves radially outward, the front portion of the lens capsule moves with posterior movement 43 such that the anterior optical surface of the lens moves posteriorly and decreases curvature so as to bring the image of the far object into focus on the retina.

With presbyopia, the inner components of the lens such as the cortex 24 may stiffen, such that the amount of accommodation decreases. The amount of anterior movement 42 of lens 22 and the amount corresponding curvature change decreases such that the eye is no longer capable of bringing both near and far objects into focus with accommodation.

Figure 1C:
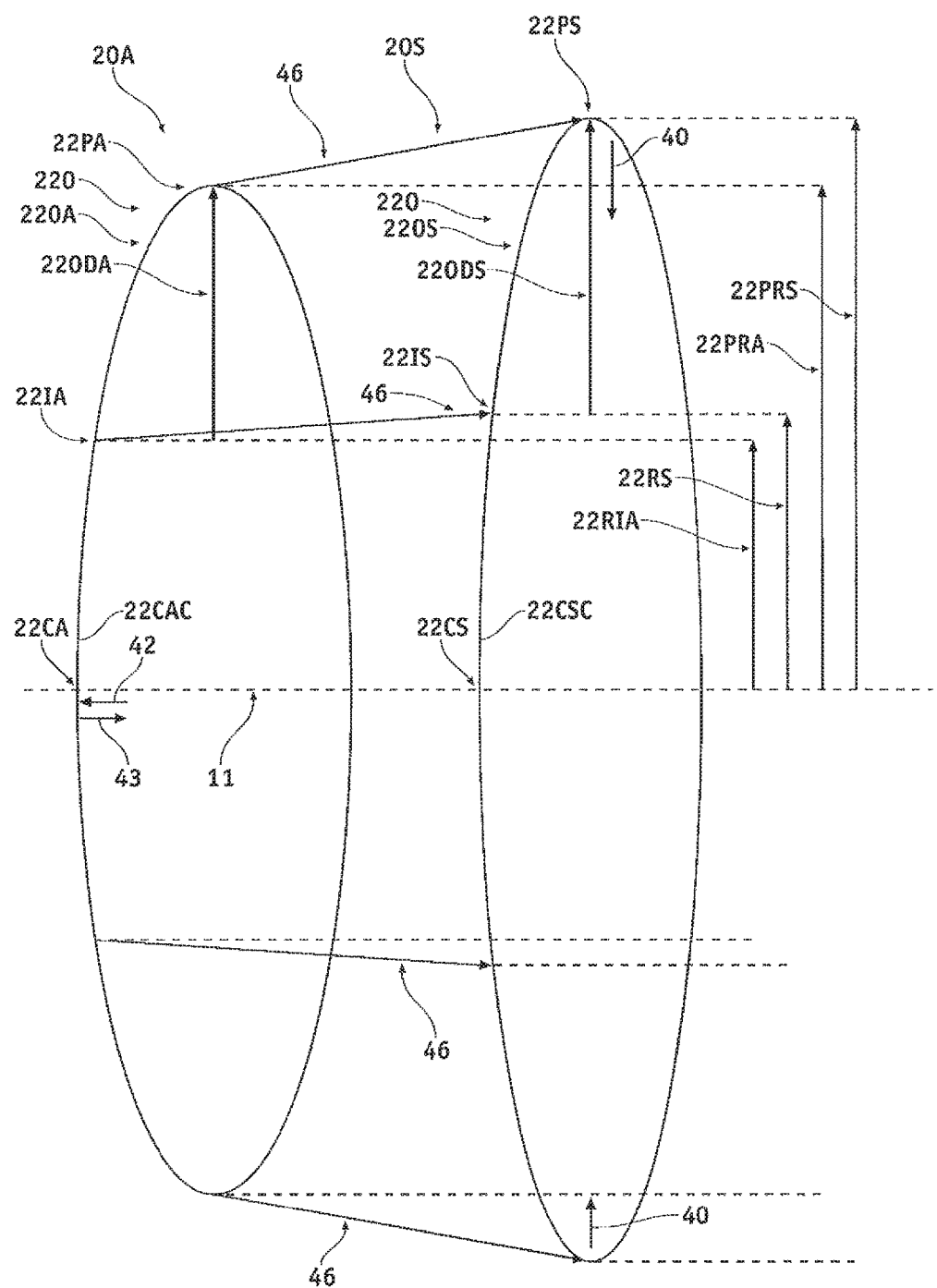
FIG. 1C shows elastic stretching of the lens capsule of the eye as in FIGS. 1A and 1B, suitable for incorporation in accordance with embodiments as described herein.

FIG. 1C shows elastic stretching of the lens capsule 22 of the eye as in FIGS. 1A and 1B, suitable for incorporation in accordance with embodiments. The lens of the eye comprises a first relaxed configuration 20A of the lens capsule for accommodation, and a second stretched configuration 20S of the lens capsule for far vision. The first relaxed configuration 20A corresponds to constriction of the ciliary muscle 32 such that tension on zonules 30 is decreased such that and the lens can relax and move forward with anterior movement 42. The second stretched configuration 20S corresponds to radially outward stretching of the lens when the ciliary muscles of the eye relax and the zonules attached to the peripheral portion 20P stretch the lens capsule and move the lens radially outward, such that and the lens can stretch and move with posterior movement 43. The correspondence of locations of lens 20 for the relaxed lens configuration 20A for accommodation and the stretched lens configuration 20S are shown with arrows 46.

The lens 20 stretches when the ciliary muscles relax such that the capsule is stretched radially outward. The relaxed lens configuration 20A for accommodation for near vision has a central portion 22C of the lens capsule 22, an intermediate portion 22IA, and a peripheral portion 22AP. The relaxed configuration 20A for accommodation comprises the central portion 22CA located along axis 11, the intermediate portion 22IA located a radial distance 22RIA from axis 11 and the peripheral portion 22PA located a radial distance 22PRA from axis 11. The relaxed configuration 20A comprises an outer portion 22OA extending from the intermediate portion 22IA to the peripheral portion 22PA with a distance 22ODA. The central portion 22CA has a curvature 22CAC when the lens comprises the relaxed configuration for accommodation.

The stretched lens configuration 20S for far vision has a central portion 22CS of the lens capsule 22, an intermediate portion 22IS, and a peripheral portion 22AS. The stretched lens configuration 20S for far vision comprises the central portion 22CS located along axis 11, the intermediate portion 22IS located a radial distance 22RIS from axis 11 and the peripheral portion 22PS located a radial distance 22PRS from axis 11. The stretched configuration 20S comprises an outer portion 22OS extending from the intermediate portion 22IS to the peripheral portion 22PS with a distance 22ODS. The central portion 22CS has a curvature 22CSC when the lens comprises the stretched configuration for far vision.

The stretching of lens capsule 22 with lens configuration 20S can store energy and provide an increased amount of radially inward force 40, so as move the anterior capsule forward with anterior movement 42. The stretching of lens capsule 42 extends from axis 11 to peripheral portion 22P. The radial distance 22PRS is greater than the radial distance 22PRA, corresponding to stretching of the central portion 22C, the intermediate portion 22I, the outer portion, and the peripheral portion 22P. The radial distance 22RIS is greater than the radial distance 22RIA corresponding to stretching of the intermediate portion 22I and central portion 22C. The radial distance 22ODA is less than the radial distance 22ODS corresponding to stretching of the outer portion 22O located between intermediate portion 22I and peripheral portion 22P. Although the stretched components of the lens capsule can move the peripheral portion 22P radially inward with the force 40, the presbyopic lens can be stiffer than the non-presbyopic lens such that the anterior movement 42 and the corresponding curvature change may not be enough to provide accommodation.

Figure 2A:
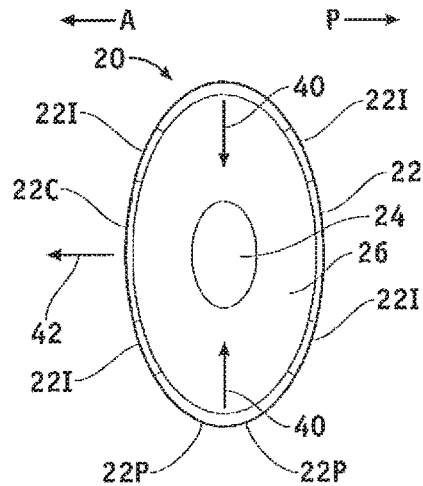
FIG. 2A shows an eye having an intermediate portion of the anterior lens capsule and an intermediate portion of the posterior lens capsule stiffened to increase accommodation, in accordance with embodiments of the present invention.

FIG. 2A shows a side view of eye 10 having an intermediate portion 22I of the anterior lens capsule and an intermediate portion of the posterior lens capsule stiffened so as to increase accommodation. An intermediate portion 22I of the lens capsule 20 is stiffened with treatment so as to increase accommodation of the patient. The intermediate portion 22I is disposed between an inner central portion 22C and a peripheral portion 22P attached to the zonules. The intermediate portion 22I may extend completely around the central portion 22C so as to define the central portion 22C with the inner boundary of the intermediate portion 22I. The intermediate portion 22I may comprise a ring, or annular oval, extending around the central portion so as to enclose the central portion. The eye comprises an anterior orientation A toward the cornea and a posterior orientation P toward the retina.

The inner central optical portion 22C comprises an optically useful portion of the lens capsule 22, and corresponds to light transmitted through the pupil of the eye. The intermediate portion 22I can be located away from the central portion 22C such that the central portion remains optically clear and substantially free from aberrations and light scatter. The intermediate portion may correspond to a portion of the capsule covered by the pupil, for example in bright light. In many embodiments, the intermediate portion is covered by the pupil in dim illumination, for example, such that the patient can receive the benefit of increased accommodation when reading in dim light or viewing objects in dim light for example. The intermediate portion may comprise an intermediate portion of the anterior capsule, or an intermediate portion of the posterior capsule, or both, for example.

The thickness of the treated intermediate portion 22I can be maintained substantially, such that the treated intermediate portion substantially resists and decreases radial movement. The resistance and decreased radial movement can improve coupling and increase radial forces of the peripheral portion of the lens capsule to the central portion of the lens capsule. As radial stretching of the intermediate portion 22I can correspond to an increase circumference of the stretched intermediate portion, the stiffened intermediate portion may comprise an annular shape such as a ring or oval extending circumferentially and substantially continuously around the central portion, so as to enclose the central portion the such that decreased circumferential stretching of the intermediate portion can decrease the radial motion and stretching of the intermediate portion.

The stiffened intermediate portion of the capsule 22I can increase accommodation of the eye 10 in many ways. The accommodation can be increased with one or more of increased radially inward force 40 of the lens capsule, increase anterior movement 42 of the lens capsule, increased curvature 22AC of the lens capsule, or increased curvature 22CPC of the central portion comprising a protrusion 22CP (FIG. 2A-3), or combinations thereof. With the stiffened portion 22I, the radially inward force 40 can be increased when the ciliary muscles of the eye contract and the zonules allow the peripheral portion of the capsule to move inward. The increased radially inward force 40 can provide increased amount of the anterior movement 42 of the lens capsule. The increased anterior movement 42 of the lens may provide an increased curvature 22CAC of the central portion 22CA when the lens accommodates so as to increase accommodation of the eye. Also, the increased anterior movement 42 of the lens capsule may provide increased accommodation based at least partially on an increased distance from the central portion 22C of the lens capsule to the retina. Alternatively or in combination, the increased forward axial movement 42 may provide protrusion 22CP having increased curvature 22CPC when the eye accommodates as described herein with reference to FIG. 2A-3, for example.

Figures 2, 2A:
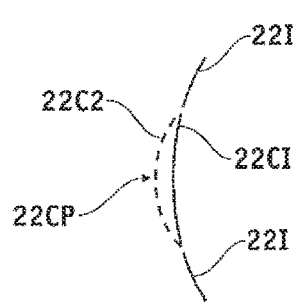
Figures 1, 2A:
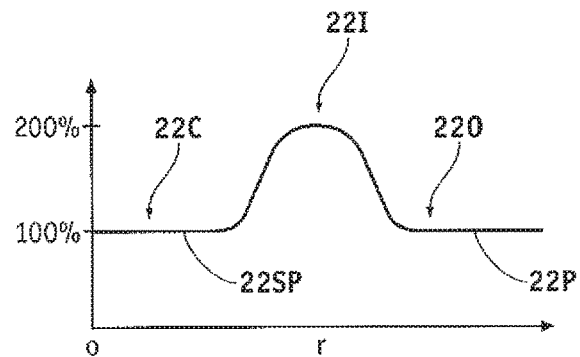

FIG. 2A-1 shows a stiffness profile 22SP of lens capsule 22C, in accordance with embodiments. The stiffness profile 22SP is shown in radial coordinates extending from a central value of zero near a center of the lens capsule to the peripheral portion 22P of the lens capsule. The stiffness profile 22SP may correspond to a percent stiffness of the lens capsule after treatment to the stiffness of the lens capsule 22C prior to treatment. The central portion 22C and the outer portion 22O may each have a substantially unchanged stiffness before and after treatment corresponding to a post-treatment stiffness of one hundred percent. The stiffness profile 22SP of the intermediate portion 22I may correspond to a graded change in the amount of stiffness, such that the stiffness profile 22SP comprises a peak stiffness. The stiffness profile 22SP corresponding to intermediate portion 22I can extend from the peak to the untreated portions with a graded amounts of relative stiffness.

The stiffening treatment as described herein can increase the modulus, for example the Young's modulus of the lens capsule of the intermediate portion 22I. The lens capsule may comprise a Young's modulus within a range from about 1.5 mN/mm2 to about 3 mN/mm2, for example. (See Weeber H A., Martin H. The Role of the Capsular Bag in Accommodation. In: Guthoff R, Ludwig K, eds. Current Aspects of Human Accommodation II. Heidelberg: Kaden Verlag; 2003). Although the material properties of the lens capsule can be at least somewhat non-linear and the Young's modulus of the lens capsule can vary with age, a person of ordinary skill in the art can determine empirically the thickness and corresponding modulus based on the teachings described herein, so as to provide stiffening treatment to the intermediate portion 22I and increased accommodation.

The intermediate portion of the lens capsule can be stiffened an amount sufficient to increase accommodation, for example increased by at least about 50%. In many embodiments, the stiffening of the lens capsule may comprise at least about 100% stiffening so as to increase accommodation of the eye. The stiffening of the intermediate portion of the lens capsule can be achieved without substantially shrinking the treated tissue, so as to decrease changes in far vision refraction of the eye. The non-substantial shrinkage of the capsule may corresponds to a change in distance refraction of no more than about 1D. The treatment of the lens capsule can maintain thickness of the lens capsule when stiffened, such that the stiffened intermediate portion can resist radial movement and decrease movement radially so as to improve coupling increase radial forces of the peripheral portion of the lens capsule coupled to the lens disposed at least partially within the capsule. As the amount of radial force to stretch the lens capsule radially outward and the corresponding radially inward force available to move the lens during accommodation can be related to the thickness of the lens capsule and the modulus of the lens capsule, substantially maintaining the thickness of the lens capsule to within about +/−30% of the thickness prior to treatment when the lens capsule is stiffened can improve coupling and increase radial forces of the peripheral portion to the lens components located at least partially within the lens capsule and increase radially inward forces to the lens components. In many embodiments the thickness of the stiffened tissue can be maintained to within about +/−20%, for example to within about +/−15%. The treated intermediate portion 22I may comprise a substantially continuous treatment region extending substantially around, for example completely around, the central portion 22C so as to enclose the central portion 22C within the capsular treatment region comprising intermediate portion 22I.

As the shrinkage of the treated intermediate portion of the lens capsule may correspond to nearsightedness, amounts of shrinkage corresponding to about 1D of induced nearsightedness in conjunction with about a 1D increase in accommodation can produce a successfully result. For example, a patient who is emmetropic prior to surgery that undergoes treatment and becomes −1 D nearsighted with far vision and can accommodate 1D can bring an object that is about ½ meter away into sharp focus.

FIG. 2A-2 shows increased curvature of the anterior lens capsule when the eye accommodates with the intermediate portion of the lens capsule stiffened to increase accommodation. The central portion of the lens capsule may comprise a first curvature profile 22C1 when the eye does not accommodate, for example when the lens capsule is stretched as described herein. The second curvature profile 22C2 may correspond to the elevation profile of a protrusion 22CP of the central portion when the eye accommodates with the intermediate portion stiffened, for example when the peripheral and outer portions of the lens capsule are not stretched and the eye accommodates. When the eye having the intermediate portion stiffened accommodates with radially inward movement of the peripheral portion 22P, the stiffened intermediate portion 22I can direct the curvature change to the non-stiffened central portion 22C, such that the central portion 22P moves anteriorly a greater amount than intermediate portion 22I. This anterior movement of the central portion 22P an amount greater than intermediate portion 22I may correspond to a bulging of the central portion 22P so as to provide protrusion 22CP and increase curvature of the central portion 22P. The central portion having protrusion 22CP has the increased change in curvature corresponding to increased optical power of the central portion 22C.

Figure 2B:
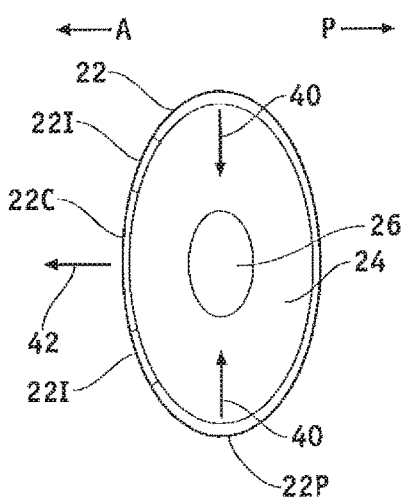
FIG. 2B shows a side view of an eye having an intermediate portion of the anterior lens capsule stiffened to increase accommodation, in accordance with embodiments of the present invention.
Figures 2, 2A, 3:
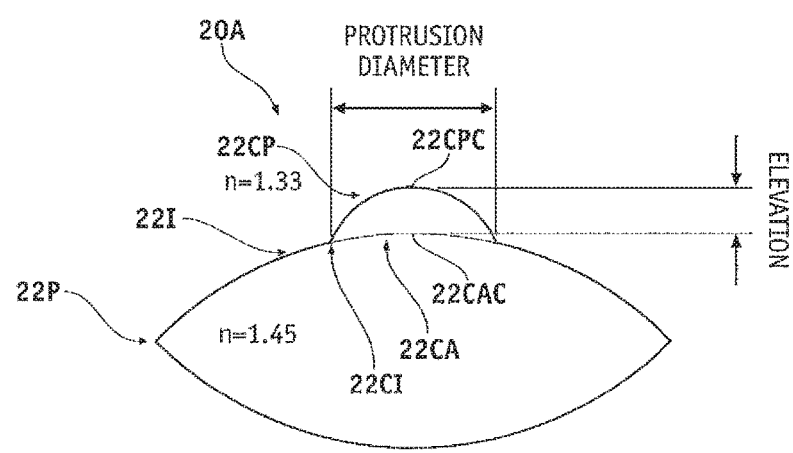
Figures 2, 2A, 3, 4:
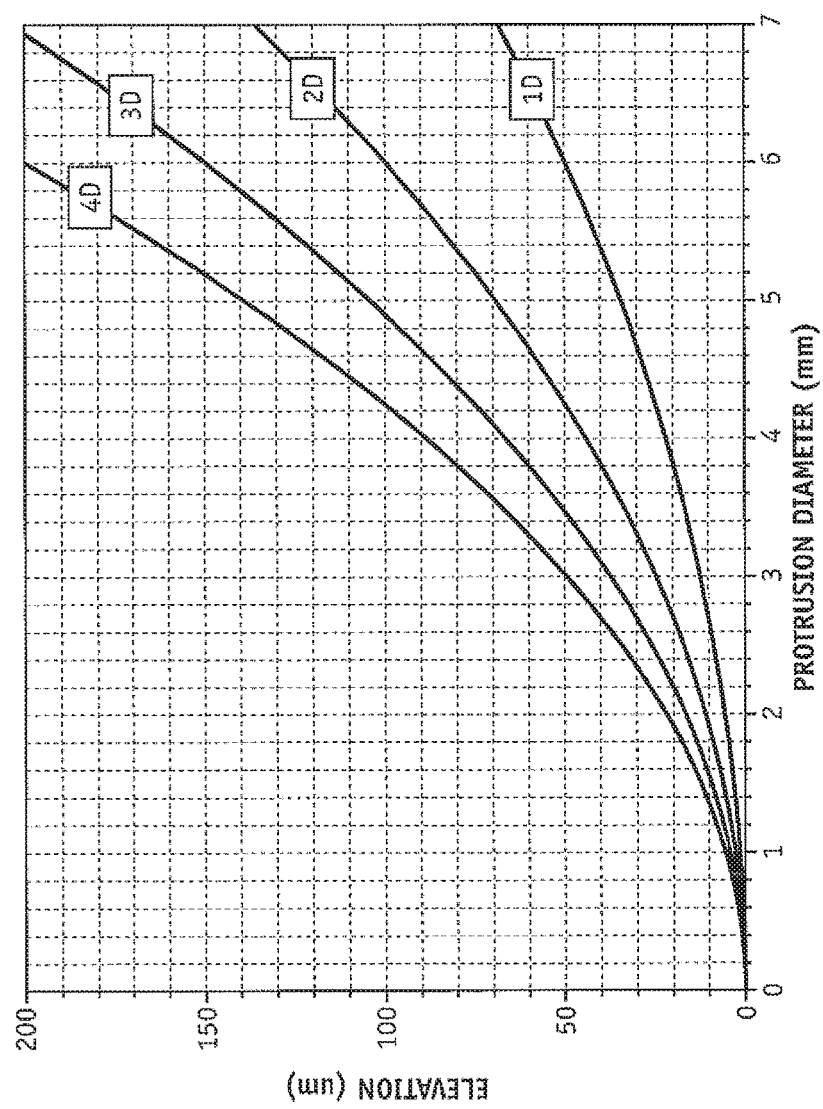

FIG. 2A-3 shows the diameter, elevation and increased optical power corresponding to the curvature 22CPC of the protrusion 22CB when the eye accommodates with the stiffened intermediate portion 22I of the lens capsule. The lens 20 has a configuration 20A for accommodation with the outward tension of the zonules decreased such that lens capsule relaxes and the peripheral portion 22P has moved radially inward. The protrusion 22CP of the central portion 22C has an elevation relative to a reference surface profile comprising the surface of the central portion 22CA when the eye accommodates naturally as described above without the stiffening treatment of the intermediate portion 20I. The elevation of the central portion 22C comprising protrusion 22CP may comprise an inflection 22CI extending around the protrusion 22CP where the curvature of the lens capsule may change abruptly and the stiffened intermediate portion 22I couples the central portion 22C. Alternatively to the abrupt change in curvature, the curvature near inflection 22CI can increase gradually with a graded transition profile such that the central portion 22C comprises a prolate elevation profile so as to correct spherical aberration of the eye.

The boundary of central portion 22CP and intermediate portion 22I may comprise a smooth graded change in curvature and profile, for example when the intermediate portion receives treatment so as to provide the graded stiffness profile. The graded stiffness profile may provide the curvature near inflection 22CI that increases gradually such that the central portion 22CP comprises the prolate elevation profile The increased elevation and curvature of the central portion relative to the peripheral portion can increase the optical power of the central portion substantially. The lens has an index of refraction of about 1.45 and the aqueous humor has an index of refraction of about 1.33, such that the curvature of the central portion 22C provides optical power. The optical power of the protrusion can be determined based on the curvature corresponding to the height and diameter of the protrusion 22CP.

FIG. 2A-4 shows the increased optical power corresponding to curvature 22CPC for varying diameters and elevations of the protrusion 22CP when the eye accommodates. The elevation of the protrusion is proportional to the optical power in Diopters (D) and to the square of the protrusion dimension across, for example a diameter across for a spherical protrusion. The diameters and corresponding elevations so as to provide curvature changes corresponding 1 D, 2 D, 3 D and 4 D of accommodation are shown in Table I. For a curvature corresponding to the 1 D protrusion having a diameter of 5 mm, the elevation is about 35 um. For a curvature corresponding to a 2 D protrusion having the 5 mm diameter, the elevation is about 70 um. A comparison of the elevation of the 1 D protrusion to the 2 D protrusion shows the approximately linear relationship of optical power to protrusion elevation. For a 1 D protrusion having a diameter of about 3 mm, the elevation is about 12 um. For the 1 D protrusion having a diameter of about 6 mm the elevation is about 50 um. A comparison of the 1 D protrusion having the diameter of 3 mm to the 1 D protrusion having the diameter of about 6 mm shows that the elevation is approximately proportional to the square of the diameter. Based on the dimensions shown, a protrusion 22CP having an exemplary 4 mm diameter and a height of about 45 um can have an increased curvature so as to provide about 2D of additional accommodative optical power.

TABLE I

Diameters and corresponding elevations to provide curvature changes corresponding 1 D, 2 D, 3 D and 4 D of increased accommodation.

| Diameter mm | Elevation @ 1 D | Elevation @ 2 D | Elevation @ 3 D | Elevation @ 4 D |
|---|---|---|---|---|
| 0 | 0 | 0 | 0 | 0 |
| 0.5 | 0.347 | 0.694 | 1.04 | 1.39 |
| 1 | 1.39 | 2.78 | 4.17 | 5.56 |
| 1.5 | 3.13 | 6.25 | 9.38 | 12.5 |
| 2 | 5.56 | 11.1 | 16.7 | 22.2 |
| 2.5 | 8.68 | 17.4 | 26.0 | 34.7 |
| 3 | 12.5 | 25 | 37.5 | 50 |
| 3.5 | 17.0 | 34.0 | 51.0 | 68.1 |
| 4 | 22.2 | 44.4 | 66.7 | 88.9 |
| 4.5 | 28.1 | 56.3 | 84.4 | 112.5 |
| 5 | 34.7 | 69.4 | 104.1 | 138.9 |
| 5.5 | 42.0 | 84.0 | 126.0 | 168.1 |
| 6 | 50 | 100 | 150 | 200 |
| 6.5 | 58.6 | 117.4 | 176.0 | 234.7 |
| 7 | 68.1 | 136.1 | 204.1 | 272.2 |

The additional optical power provided by protrusion 22CP can be combined with anterior movement of the central portion 22C and the intermediate portion 22I, so as to further increase the amount of accommodative optical power when protrusion 22CP increases curvature of the central portion 22C. For example, increased stretching of the peripheral and outer portions of the lens capsule can be combined with the protrusion 22CP and the anterior movement of the intermediate portion 22I and central portion 22C, so as to provide greater than about 2D of accommodative optical power when the protrusion 22P provides about 2D of accommodative optical power.

FIG. 2B shows a side view of the eye 10 having intermediate portion 22I of the anterior lens capsule stiffened to increase accommodation. This stiffening of the anterior capsule can be less invasive than stiffening the posterior capsule, for example, and can be used in many embodiments that comprise increasing the amount of accommodation of natural lens of the eye, for example.

Figure 2C:
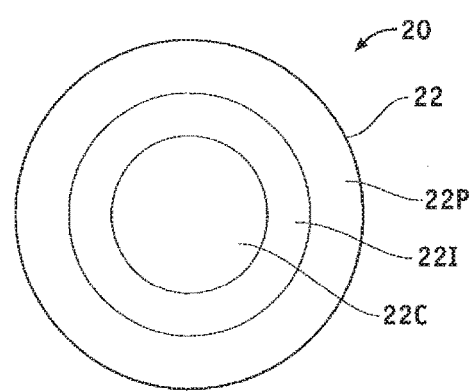
FIG. 2C shows a front view the eye having an intermediate portion of the anterior lens capsule stiffened to increase accommodation as in FIG. 2B.

FIG. 2C shows a front view the eye having intermediate portion 22I of the anterior lens capsule stiffened to increase accommodation as in FIG. 2B. The central portion 22C may comprise a distance across such as a diameter. The distance across the central portion 22C can be defined by the treatment of the intermediate portion and can be within a range from about 1.5 mm to about 6 mm, for example. The dimensions of the central portion 22C may correspond to dimensions of the pupil, for example within a range of about 2 mm to about 6 mm, for example within a range from about 3 mm to about 5 mm, so as to correspond to dimensions of the presbyopic pupil. The intermediate portion 22I comprises a distance across, for example an inner annular diameter and an outer annular diameter. The inner annular diameter may correspond to the size of the central portion 22C. The outer annular dimension of the intermediate portion 22I may correspond to an outer diameter of treatment, for example. The outer annular dimension may correspond to a dimension of the dilated pupil with cycloplegia, for example, such that the intermediate portion can be accessed readily during surgery, for example when the pupil is dilated during surgery. The peripheral portion 22P may comprise a substantially untreated portion of the lens capsule coupled to the zonules of the eye such that the peripheral portion can stretch elastically. Based on the teachings described herein, a person of ordinary skill in the art can determine dimensions of the intermediate portion so as to increase accommodation and decrease presbyopia with the natural lens of the eye, for example. The anterior capsule when treated may comprise similar dimensions, for example.

Figure 2D:
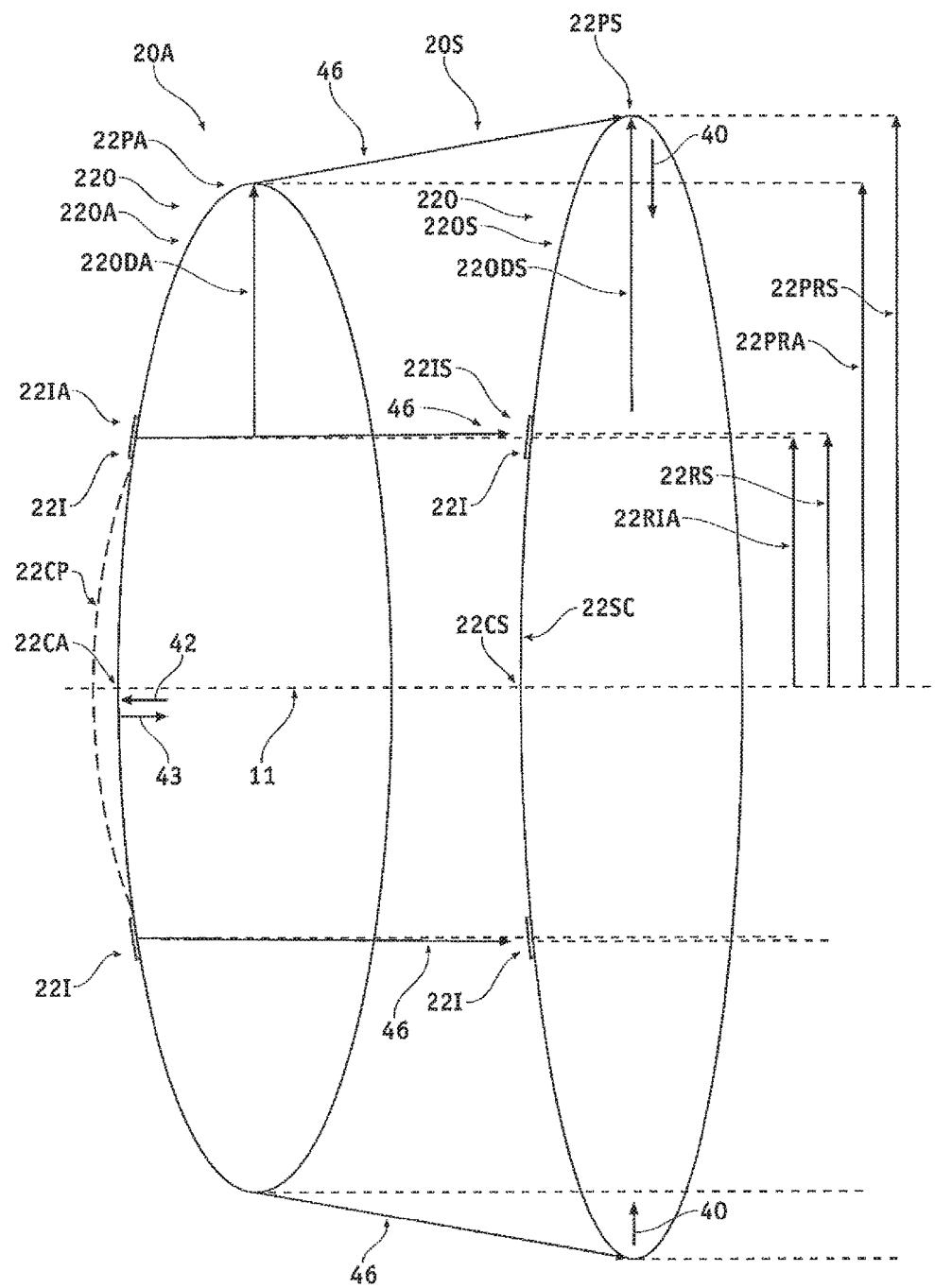
FIGS. 2D and 2E show side and front views, respectively, of the eye having the support coupled to the intermediate portion of the eye to increase elastic stretching of the lens capsule to the decrease presbyopia as in FIGS. 2B and 2C.
Figure 2E:
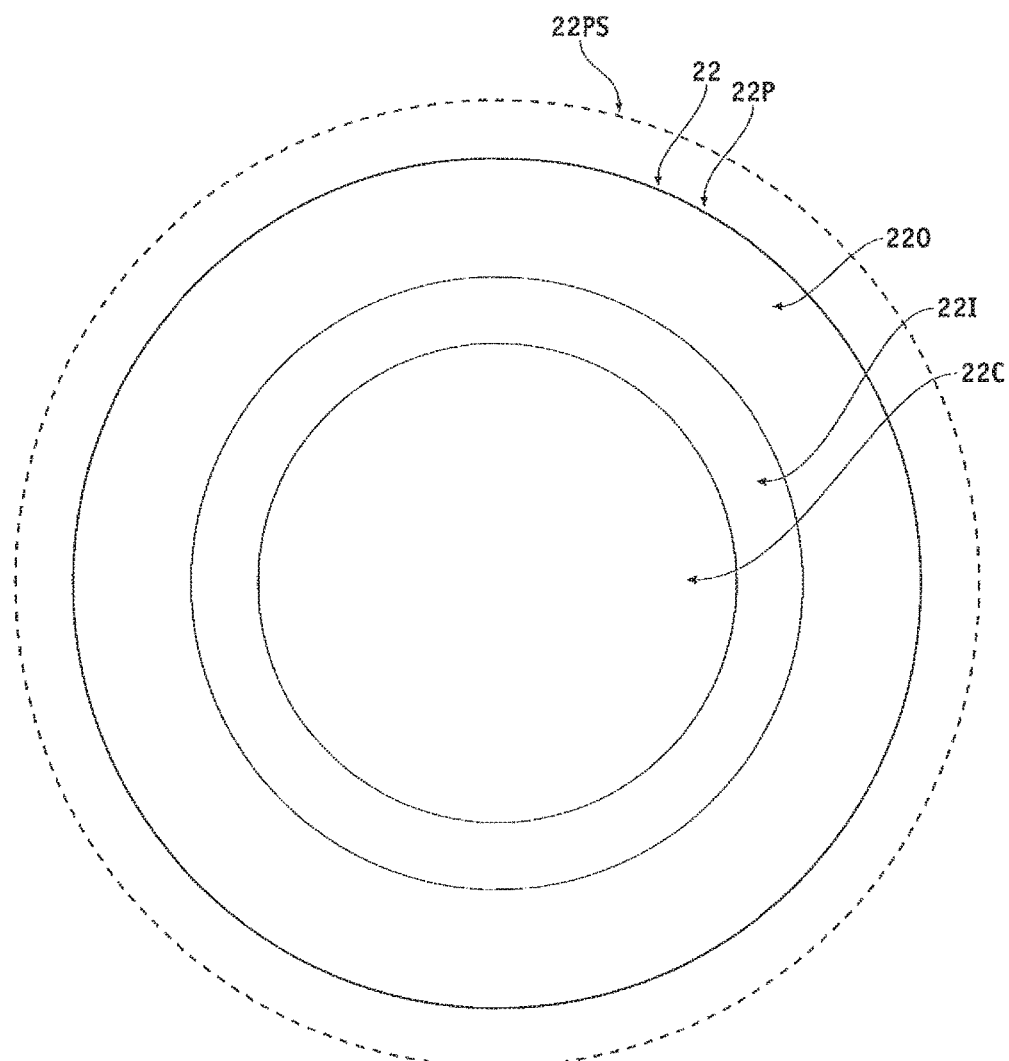

FIGS. 2D and 2E show side and front views, respectively, of the eye having the stiffened intermediate portion of the capsule to increase elastic stretching of the lens capsule to the decrease presbyopia. The intermediate portion 22I of the lens capsule can be stiffened such that the strain of the intermediate portion corresponds to the relaxed capsule during accommodation so as to increase stretching of the outer portion 22O of the lens capsule when the ciliary muscle relaxes and the capsule is stretched with the zonules.

The increased stretching of lens capsule 22 with lens configuration 20S can store energy and provide an increased radially inward force as indicated by arrows 40, so as to increase curvature and move the anterior capsule forward as indicated with arrow 42. The increased stretching of lens capsule 42 corresponds to increased stretching of outer portion 22O of the capsule between the stiffened intermediate portion 22I and the peripheral portion 22P coupled to the zonules. The radial distance 22RIS is similar to radial distance 22RIA corresponding to no substantial increased stretching of the intermediate portion 22I and central portion 22C. The radial distance 22ODA is less than the radial distance 22ODS corresponding to stretching of the outer portion 22O located between intermediate portion 22I and peripheral portion 22P. As the peripheral portion 22P of the lens may be pulled that radial distance 22PRS corresponds substantially to the eye without the stiffening treatment as shown above, the radial stretching distance 22ODS can be substantially greater for the eye with the stiffened intermediate portion 22I.

The intermediate portion of the lens capsule can be treated with amounts of strain corresponding to the relaxed lens capsule during accommodation, or amounts of strain corresponding to stretching of the lens capsule when the ciliary muscle of the eye relaxes for far vision, and amounts in between. For example, with capsulorhexis, it can be helpful to stiffen the tissue around the edge of the capsulorhexis incision when the eye is dilated and corresponds to a stretched lens capsule. With the natural crystalline lens of the eye, the amount of strain of the intermediate portion 22I and the central portion 22C can be related to the elevation of protrusion 22CP. The decreased radial movement and decreased circumferential stretching of intermediate portion 22I can define an outer boundary of protrusion 22CP and encourage formation of protrusion 22CP.

The curvature profile elevation data and figures as described herein show that presbyopia can be treated with an appropriately sized intermediate portion 22I so as to produce a protrusion to treat presbyopia, and that the protrusion can be used in combination with additional components of accommodation, such as movement anteriorly of the intermediate portion 22I and the central portion 22C when the eye accommodates, and radially inward elastic force and radially inward movement of the peripheral portion of the lens capsule. The elastic peripheral and outer portions of the lens capsule can move the intermediate and central portions of the lens capsule anteriorly when the eye accommodates, and the elastic peripheral and outer portions of the lens capsule can provide radially inward force and radially inward movement of the peripheral portion of the lens capsule to move the intermediate portion 22I and the peripheral portion 22P anteriorly. The intermediate portion 22I can be stiffened with an amount of strain to provide appropriate far vision refraction and increased accommodation. The amount of strain of the stiffened intermediate portion may correspond to the stretched lens capsule for far vision, the non-stretched accommodating lens capsule, or amounts of strain in between corresponding to intermediate vision. In many embodiments, the intermediate portion 22I is stiffened when the eye does not accommodate and the lens capsule is stretched, for example when dilated during surgery, such that the intermediate portion 22I and the central portion 22C comprise a curvature and strain corresponding to the non-accommodating stretched lens capsule for far vision of the eye. Alternatively, the intermediate portion 22I can be stiffened with amounts of strain corresponding substantially to the non-stretched capsule when the eye accommodates, for example, such that the intermediate portion 22I and the central portion 22C comprise a curvature and strain corresponding to the non-stretched accommodating lens capsule.

Figure 2F:
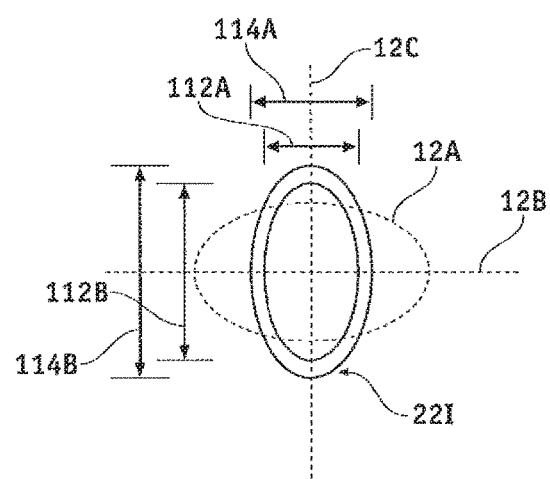
FIG. 2F shows the support comprising an oval shape to correct astigmatism of the eye, in accordance with embodiments.

FIG. 2F shows a view along the axis 11 of the stiffened intermediate portion 22I comprising an oval shape to correct astigmatism of the eye. The oval shape profile may comprise one or more of an elliptical shape, a lentoid shape, or an asymmetrical elliptical shape, extending substantially around central portion 22C such that protrusion 22CP comprises a substantially toric shape when the eye accommodates to as to correct the astigmatism of the eye. The astigmatism of the eye may comprise lenticular astigmatism or corneal astigmatism. For example, the astigmatism may comprise corneal with the rule astigmatism corresponding to a toric corneal shape having a steeper corneal curvature along a substantially vertical axis 12C and a flatter corneal curvature along a substantially horizontal axis 12B, such that a depth contour plot of the toric cornea shows ellipses such as ellipse 12A having a short axis extending along vertical axis 12C and long axis 12B perpendicular vertical axis 12C. Merely by way of example, the curvature of the cornea along axis 12B can correspond to an optical power of about 43D, and the curvature of the cornea along axis 12C can correspond to an optical power of about 44D, for example.

The long dimension of the oval intermediate portion 22I can be aligned with the astigmatism of the eye such as with the rule astigmatism, so as to correct the vision of the eye. For example, the long dimension of the oval intermediate portion 22I can be aligned with the steeper substantially vertical axis 12C, and the shorter dimension of the oval intermediate portion 22I can be aligned with the flatter substantially horizontal axis 12B. The oval protrusion 23P can have a ratio of the long axis to the short axis so as to correct the astigmatism of the eye when the lens capsule is relaxed with ciliary muscle contraction and the eye accommodates for near vision, or when the lens capsule is stretched with the zonules and the ciliary muscle is relaxed for far vision.

The stiffened oval intermediate portion 22I can induce astigmatism of the lens with toric protrusion 22CP so as to correct the astigmatism of the eye. The oval intermediate portion 22I coupled to annular oval support 100 comprises a shorter inner dimension 112A and a shorter outer dimension 114B. The oval stiffened intermediate portion 22I comprises an elongate inner dimension 112B and an elongate outer dimension 114B. The shorter inner dimension 112A and the elongate inner dimension 114A can define the oval outer boundary of the central portion 22C, such that the central portion 22C comprises an oval shape profile having one or more of an elliptical shape profile, a lentoid shape profile, or an asymmetrical elliptical shape profile. In many embodiments, the oval shape profile corresponds to a toric shape of the protrusion 22CP when the eye accommodates. When the lens capsule moves anteriorly with accommodation of the lens capsule such that central portion 22C comprises protrusion 22CP, the curvature change of the lens capsule can be related to the inner dimensions across the intermediate portion such as shorter inner dimension 112A and elongate inner dimension 112B. The shorter dimension 112A corresponds to a steeper curvature change of the lens capsule when the central portion moves anteriorly, and the elongate dimension 112B corresponds to a less steep change in curvature when the lens capsule moves anteriorly. The flatter curvature change along the axis of the elongate dimension 112B of the oval can correct the with the rule astigmatism along the vertical axis 12C.

The curvature 22CPC and corresponding elevation profile of the protrusion 22CP can be combined with the shorter inner dimension 112A and the elongate inner dimension 112B so as to determine the amount of optical correction of the protrusion. Alternatively or in combination, the ratio of the shorter dimension to the longer dimension and the elevation of the protrusion 23C can be used to determine the optical correction of the toric protrusion. For example, a patient can have corneal astigmatism with keratometer readings of about 43 D along an axis 180 of degrees and 44 D along an axis of 90 degrees corresponding to a refraction of the eye of about 0 D sphere −1.0 cylinder along an axis of 180 degrees. The dimensions of the short dimension and the long dimension of the oval can be sized to induce astigmatism of the lens to correct the astigmatism of the eye when the eye accommodates. For example the long dimension and the short dimension of the oval support can be sized such that the long dimension corresponds to about +1 D of optical power along axis 12C and the short dimension of the oval corresponds to about +2D of optical power along axis 12B when the eye accommodates, such that the refraction of the eye with accommodation based on the change in curvature 22CPC of the central potion 22CP is about −2 D along axis 12B and about −2 D along axis 12C.

The cylinder of the eye can be corrected with many ratios of the long and short dimensions of the oval support 100. For example, an eye having a far vision refraction of 0 D sphere −1 D cylinder at axis of 180 degrees can be corrected with the oval protrusion. The long inner dimension 112B can be aligned along the 90 degree axis and the short inner dimension 112A can be aligned along the 180 degree axis. When the protrusion elevation height is about 50 microns, the oval support may have a long dimension of about 6 mm and a short dimension of about 4.2 mm, as described above with reference to FIG. 2A-4. Many additional combinations of dimensions can be identified by a person of ordinary skill in the art based on the teachings described herein. The protrusion coupled to the oval support can provide about +2D of optical power along axis 12B and about +2D of optical power along axis 12C corresponding spherical near vision refraction of about −2 D sphere when the eye accommodates.

As the central and intermediate portions of the anterior lens capsule can move forward together so as to provide optical correction in addition to the curvature 22CPC of the protrusion 22CP, the amount of accommodation and corresponding near vision refraction of the eye can be greater than the amount provided by the curvature 22CPC of protrusion 22CP. Alternatively or in combination, the intermediate portion 22I may be coupled to support 100 so as to provide additional stretching of the outer portion 22O and peripheral portion 22P of the lens capsule as described herein, such that the accommodation can be further increased. Based on the teachings described herein, a person of ordinary skill in the art can conduct additional experiments and computer simulations so as to determine empirically the protrusion height and corresponding sizes and ratios of the short axis and the long axis so as to correct astigmatism when the eye accommodates.

As a small amount of astigmatism can be tolerated by the patient, the oval support can be used to increase the amount of accommodation of the eye and provide a small amount of astigmatism with acceptable vision, for example about 1 D astigmatism or less.

Figure 3A:
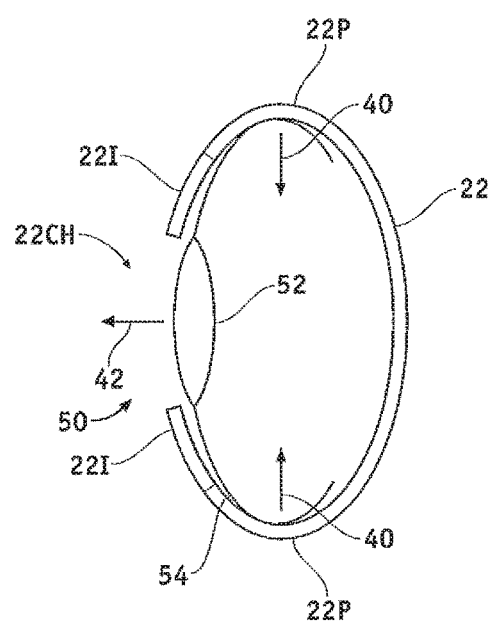
FIG. 3A shows a side view the eye having an accommodative IOL positioned substantially within a lens capsule having the intermediate portion stiffened to increase accommodation, in accordance with embodiments of the present invention.

FIG. 3A shows a side view of the eye having an accommodating IOL 50 positioned substantially within a lens capsule having the intermediate portion stiffened to increase accommodation. The accommodating IOL 50 comprises a lens 52 and a haptic 54. The radially inward force of the capsule in contact with haptic 54 as indicated with arrow 40 can move the lens 52 forward to increase optical power of the eye and increase the amount of accommodation of the accommodating lens 50.

The accommodating IOL 50 may be placed at least partially within the capsule 22. The stiffening treatment of the capsule can be combined with a capsulorhexis to remove the central portion 22C of the anterior lens capsule. The capsulorhexis can be performed during cataract surgery to remove the natural lens and allow placement of the accommodating IOL in the lens capsule. The tissue of the intermediate portion 22I can be stiffened so as to decrease radial movement of the capsulorhexis edge and increase accommodation of the accommodating IOL 50. The stiffening treatment of the intermediate portion inhibits radial motion of the intermediate portion 22I so as to increase elastic stretching of the peripheral portion 22P when the lens capsule stretches such that the peripheral portion can move the haptic with increased radially inward force as indicated with arrow 40. The stiffening treatment of the intermediate portion 22I can be performed before, during or after the capsulorhexis, or combinations thereof. For example, the intermediate portion 22I of the anterior capsule can be stiffened prior to capsulorhexis with the pupil dilated such that the curvature of the natural lens is maintained, and such that the curvature corresponds to the curvature of the non-accommodative eye. Following the capsulorhexis, the intermediate portion of the posterior capsule as shown above can be stiffened, for example.

The accommodating IOL 50 may comprise one or more components of know accommodating IOLs. The lens 52 may comprise a rigid material that provides accommodation when the lens 52 moves anteriorly. Alternatively or in combination, the lens 52 may comprise a flexible material that deforms to increase the curvature when the eye accommodates. Example of lenses having components suited for use in accordance with embodiments as described herein include the Crystalens™ HD IOL, Focus IOL™ IOL, and FlexOptic™ IOL.

Figure 4A:
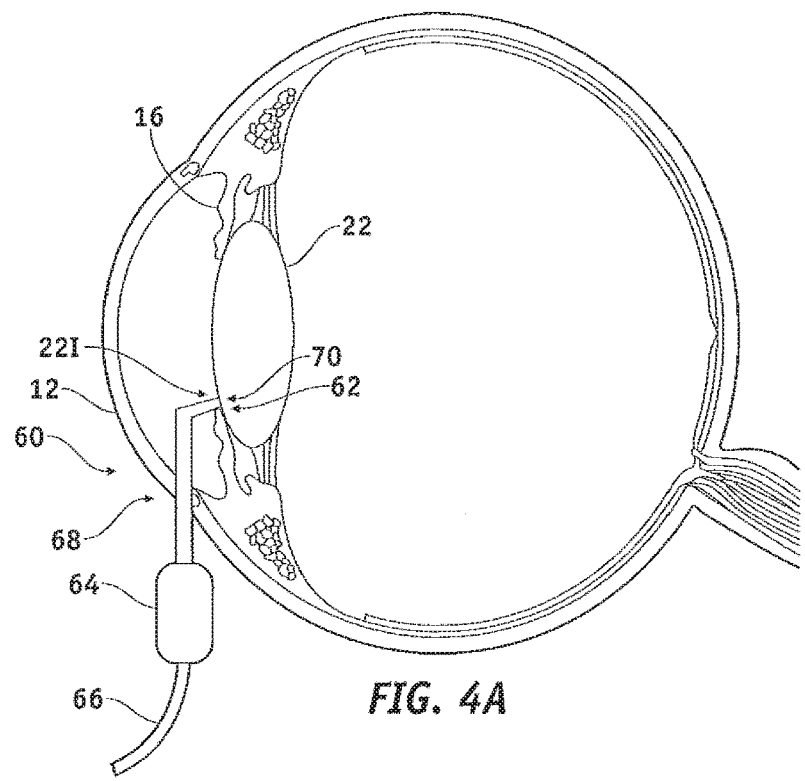
FIG. 4A shows a side view of treatment of the eye to stiffen the intermediate portion of the lens capsule with a probe, in accordance with embodiments of the present invention.

FIG. 4A shows a side view of the eye being treated to stiffen the intermediate portion of the lens capsule with a probe 60. The probe 60 may comprise a probe tip 62 at a distal end to emit one or more of an energy or an agent 70 to treat and stiffen the intermediate portion 22I. The one or more of the energy or agent 70 may comprise laser energy, mechanical energy, electrical energy such as radiofrequency or microwave, or an agent such as chemical agent or nutritional agent. The probe 60 may comprise an elongate portion 68 for insertion into the eye through an incision in the cornea 12 near a periphery of the cornea. The incision can be of any size, preferably no more than about 2 mm, more preferably no more than about 1 mm. The probe 60 may comprise an elongate handle 64 for the surgeon to grasp the probe. A cable 66 can connect the probe to a source of the one or more of the energy or agent 70 and circuitry to deliver the energy or agent 70 in accordance with a treatment profile. The probe tip 62 can be moved around the eye to treat the intermediate portion of the anterior capsule, for example. The eye may be dilated, for example with cycloplegia, so as to expose the intermediate portion 22I for treatment. The cable may comprise one or more of a channel to deliver the treatment agent, a waveguide to delivery electromagnetic energy such as fiber optic to deliver light energy, or an electrical conductor to deliver electrical RF energy to the probe tip or electrical energy to a mechanical transducer, so as to stiffen the intermediate portion 22I.

The stiffening substance may comprises one or more of an adhesive, a thermoreversible adhesive such as Poly(N-isopropylacrylamide) (hereinafter "p-Nipam"), a patterned microstructure based adhesive such as a setae based adhesive, a glycoprotein based adhesive such as a glycosylated hudroxytryptophan, a curable adhesive, a tissue fixative, a crosslinker, a photo-sensitive crosslinker, or a substance to inhibit nutrients to the intermediate portion. The setae may comprise setae similar to gecko footpads having the attractive forces that hold the setae to surfaces with van der Waals interactions between the finely divided setae and the surface of the lens capsule. The substance can be suitable for a chemical reaction, such as a photochemical reaction. The substance may comprise cross-linker, for example thiosulfate. The substance may comprise as a photosensitive cross-linker, such as riboflavin.

The probe 60 can be used in many ways to treat the intermediate portion 22I of the capsule. For example, the probe tip can be moved in a circular pattern such that intermediate portion 22I comprises an annular portion. The probe tip 62 can be moved to a plurality of treatment locations, with an amount of energy delivered to each location. The treatment profile can be configured such that tissue is stiffened at each location without substantially shrinking the tissue of the intermediate portion 22I such that the refraction of the eye when not accommodating is change less than about 1 D, for example less than about 0.5 D when treated.

Treating the intermediate portion may comprise delivering one or more of an energy or a substance to the intermediate portion. The energy may comprise one or more of mechanical energy, electromagnetic energy, RF energy, microwave energy, light energy, UV light energy, visible light energy or infrared light energy.

The agent 70 may comprise a substance such as one or more of an adhesive, a curable adhesive, a tissue fixative, riboflavin, or a substance to inhibit nutrients to the intermediate portion, for example. The adhesive may comprise one or more of cyanoacrylate adhesive, temperature sensitive adhesive, thermoreversible adhesive or setae based adhesive.

Figure 4B:
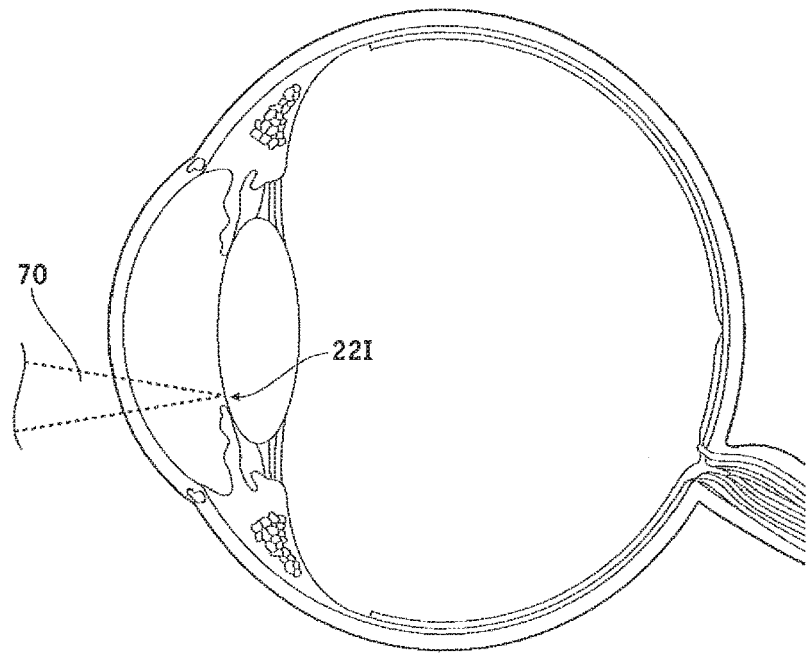
FIG. 4B shows a side view treatment of the eye to stiffen the intermediate portion of the lens capsule with a light beam, in accordance with embodiments of the present invention.

FIG. 4B shows a side view treatment of the eye to stiffen the intermediate portion of the lens capsule with a light beam. The one or more of the energy or agent 70 may comprise a light beam. The light beam may comprise a light beam focused on the intermediate portion 22I of the lens capsule, for example the anterior capsule, such that the intermediate portion is stiffened. The light beam may comprise infrared, visible, or ultraviolet energy, for example, and the light beam may comprised pulsed or substantially continuous wave (hereinafter "CW") light energy from one or more of many sources such as a laser, an LED, or a lamp.

In many embodiments, the light energy is transmitted through the cornea of the eye and absorbed with the intermediate portion to treat the intermediate portion.

Figure 4C:
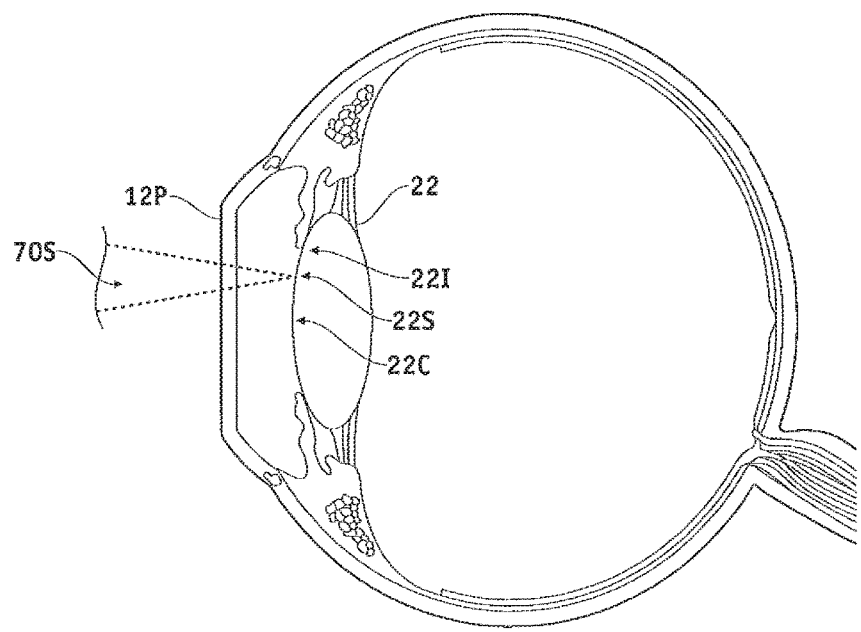
FIG. 4C shows a side view of treatment of the eye with a light beam to soften a portion of the lens capsule located between the intermediate portion and the central portion, in accordance with embodiments of the present invention.

FIG. 4C shows a side view of treatment of the eye with a light beam 70S to soften a portion 22S of the lens capsule located between the intermediate portion 22I and the central portion 22C. While many sources of light energy can be used, a femto second laser can be used at a controlled depth corresponding to treatment of the lens capsule. The stiffing treatment to the intermediate portion of the lens capsule can be combined with the softening treatment. The softening of the capsule can be accomplished by increasing the strength of the laser, increasing the number of holes or slits cut in a given area. The cuts or holes could also be done in a way as to not completely penetrate the capsule. The hole density could also be varied over the surface of the capsule to create different optical affects such as increasing spherical aberration, multifocality, coma etc. during accommodation. The holes pattern could form a ring or cold be in a bulls eye pattern or just a central dot. The procedure could be created on preferably the anterior capsule but could be accomplished on the posterior capsule or both capsules.

Figure 4D:
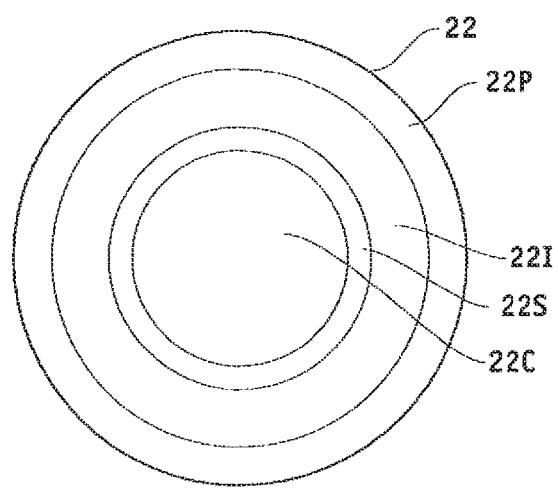
FIG. 4D shows a front view of softening treatment of the portion of the eye as in FIG. 4C.

FIG. 4D shows a front view of a softening treatment portion 22S of the eye as in FIG. 4C. The softening treatment portion 22S may comprise an annular treatment zone, for example.

Figure 4E:
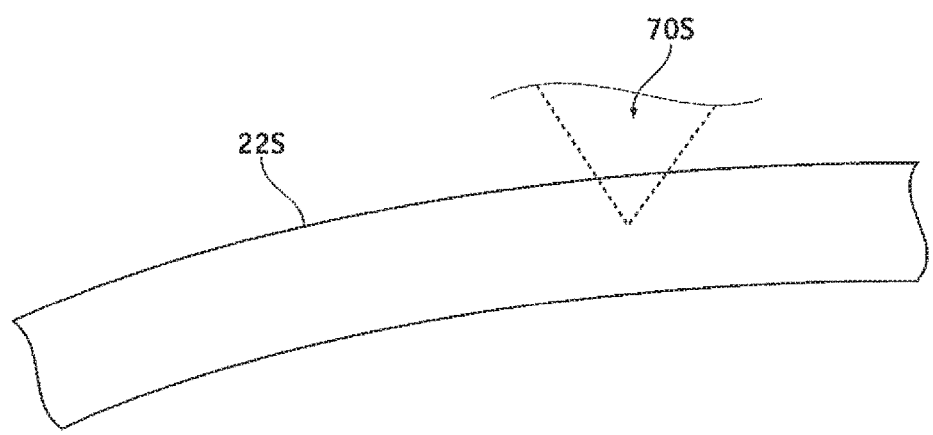
FIG. 4E shows the treatment as in FIGS. 4C and 4D located within the capsule to inhibit penetration of the capsule.

FIG. 4E shows the treatment as in FIGS. 4C and 4D located within the capsule to inhibit penetration of the capsule. The softening beam 70S may comprise a laser beam of a femto second laser, for example. Alternatively the softening beam may comprise a CW beam focused on the capsule, for example.

Figure 4F:
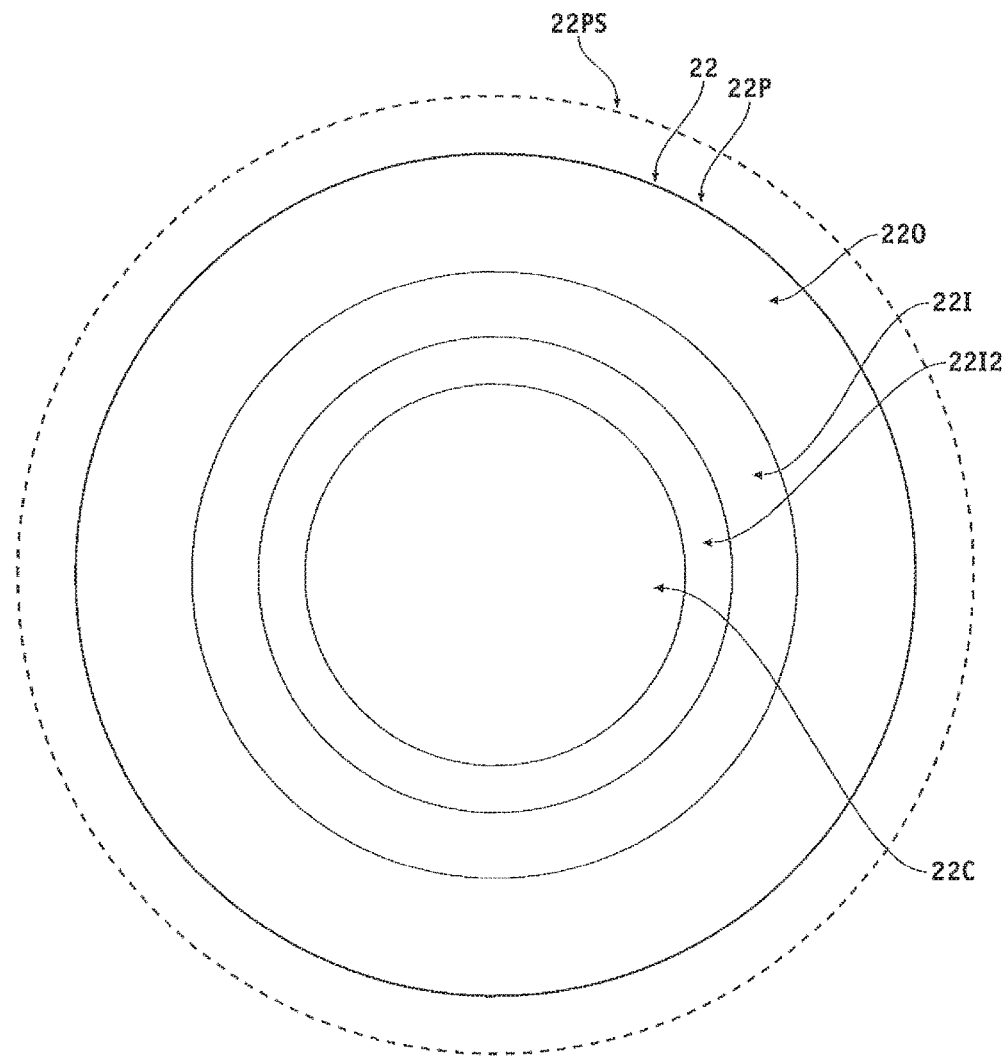
FIG. 4F shows the retreatment of the capsule, in accordance with embodiments.

FIG. 4F shows the retreatment of the capsule. The retreatment of the capsule may occur when the eye has healed and when the vision of the eye has been measured after the first treatment, for example at least about one day after the first treatment. The retreatment can be located at a second intermediate portion of the lens capsule. The second intermediate portion 22I2 of the lens capsule corresponding to the second treatment may overlap at least partially with the first intermediate portion 22I, or can be separated. The second intermediate portion 22I2 may be located radially inward of the first intermediate portion to increase the amount of accommodation or adjust the far vision refraction of the eye, for example when the first treatment under corrects the patient and additional treatment can be helpful.

Figure 5A:
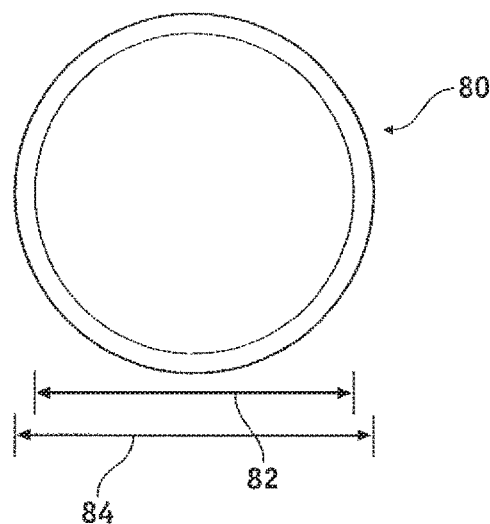
FIG. 5A shows a top view of a structure to apply an agent to the intermediate portion of the lens capsule, in accordance with embodiments of the present invention.

FIG. 5A shows a top view of a structure 80 to apply an agent to the intermediate portion of the lens capsule. The structure 80 may comprise an inner annular dimension, for example an inner annular diameter 82, and an outer annular dimension, for example an outer annular diameter 84 corresponding to the dimensions of the intermediate zone 22I. The structure may comprise an absorbent structure having an amount of the agent disposed thereon, for example.

Figure 5B:
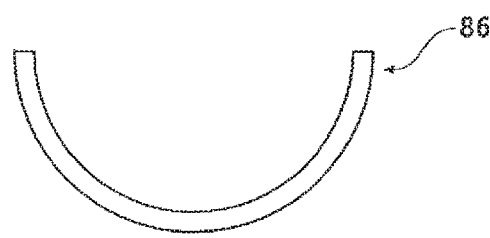
FIG. 5B shows a top view of the structure as in FIG. 5A folded for insertion through an incision, in accordance with embodiments of the present invention.
Figures 1, 5B:
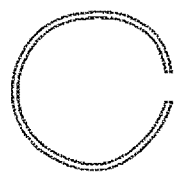
Figures 2, 5B:
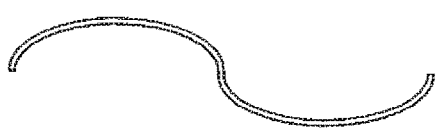
Figures 3, 5B:

FIG. 5B shows a top view of the structure 80 as in FIG. 5A folded for insertion through an incision, such that the structure 80 comprises a narrow elongate profile configuration 86 for insertion through the incision. The dimensional difference between the inner annular diameter 82 and the outer annular diameter 84 correspond to a size of the incision, for example. The folded end may be advanced through the incision first, and the structure 80 unfolded within the eye to apply the agent to the intermediate zone with contact to the capsule.

FIGS. 5B1 and 5B2 show the structure 80 comprising an expanded wide profile configuration, and narrow profile configuration for insertion into the eye through an incision in the cornea, respectively. The structure can be inserted through an incision of no more than about 2 mm, for example. The wide profile configuration may comprise an annular structure, such as a ring or oval annular structure such as a C-ring annular structure. The structure 80 can be twisted for insertion through the incision in the narrow profile configuration and can expand to the wide profile configuration and adhered to the lens capsule as described herein. The C-ring annular structure may be aligned with the lens capsule so as compensate for broken zonules, for example.

FIG. 5B3 shows a narrow profile configuration for insertion into the eye through the incision with rotation of the structure 80 shown in FIG. 5B1.

Figure 5C:
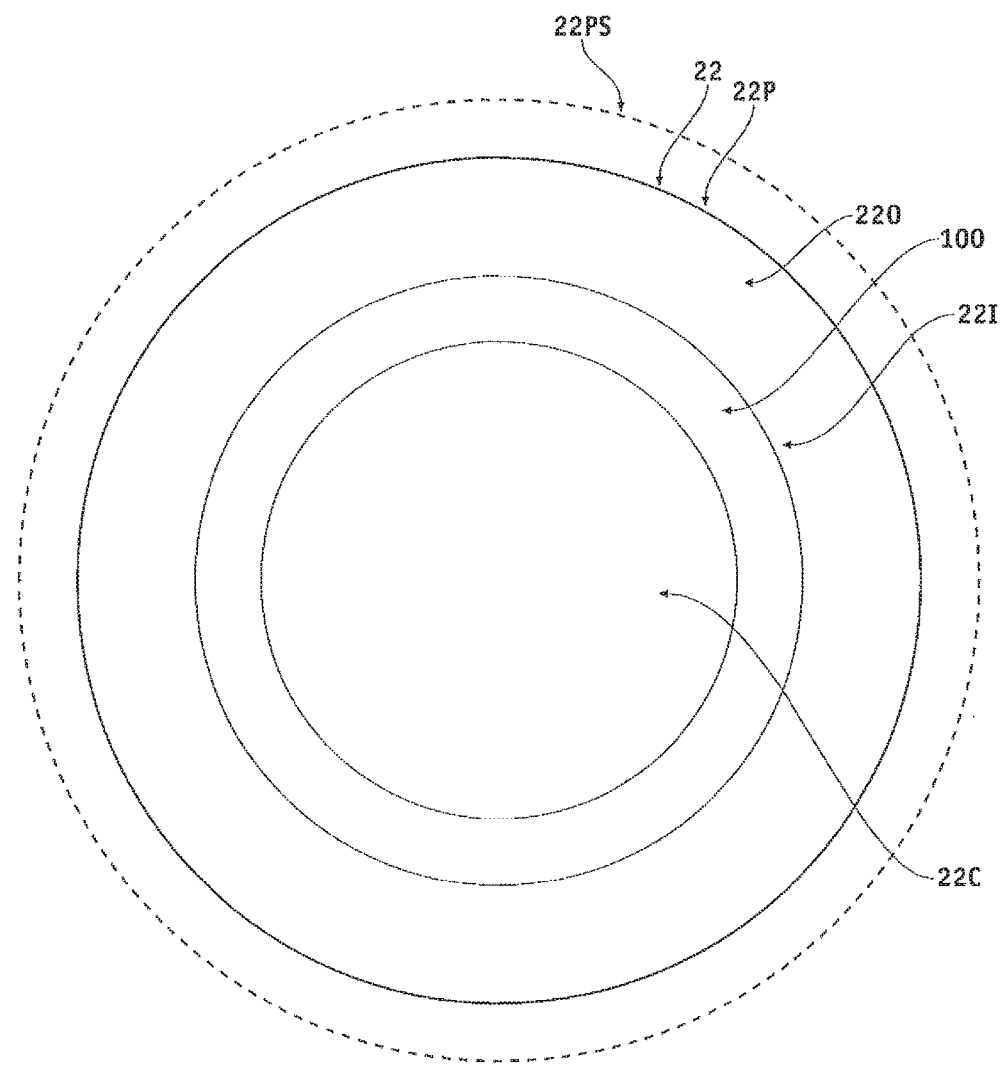
FIG. 5C shows a stiffening support coupled to the intermediate portion of the capsule to stiffen the intermediate portion with the support, in accordance with embodiments of the present invention.

FIG. 5C shows a stiffening support 100 coupled to the intermediate portion of the capsule to stiffen the intermediate portion of the capsule with the support. The treatment of the capsular tissue to stiffen the intermediate portion of the capsule may comprise coupling the stiffening support to the tissue to decrease radial movement of the capsule, such that stretching of outer portion 22O is increased. The support 100 can be coupled to the tissue of the lens capsule in many ways, for example with an adhesive or mechanical clamping or combinations thereof. The support 100 may comprise configurations, structures and insertion methods similar to structure 80 as described herein.

Figure 6A:
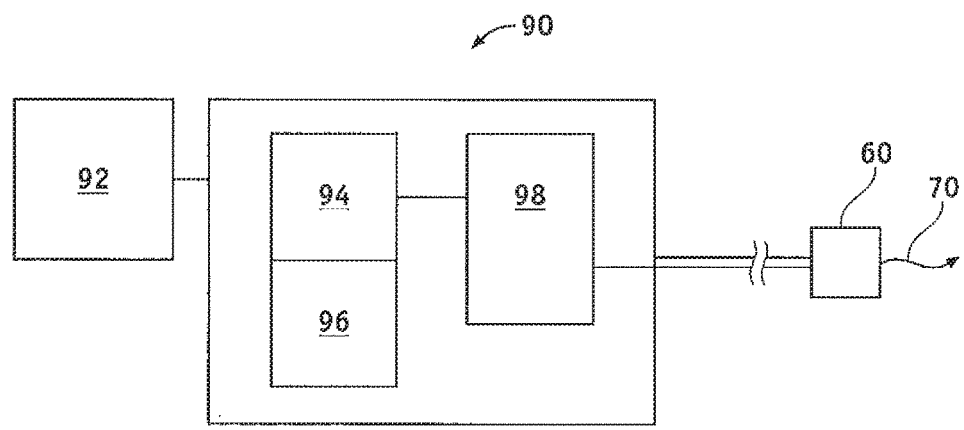
FIG. 6A shows an apparatus to apply a treatment profile to stiffen the intermediate portion of the lens capsule, in accordance with embodiments of the present invention.

FIG. 6A shows an apparatus 90 to apply a treatment profile of the one or more of the agent or energy 70 so as to stiffen the intermediate portion of the lens capsule. The apparatus 90 comprises a source 92 of energy or agent, such as a laser to generate a laser beam or a reservoir to contain an agent. The source 92 is coupled to circuitry 94 to deliver the one or more of the energy or agent in accordance with the delivery profile. The circuitry 94 may comprise a processor 96 having a computer readable medium having instructions of a computer readable medium stored thereon so as to delivery an amount of the one or more of the energy or substance 70 to the eye. The circuitry 94 is coupled to an output control 98 coupled to the probe 60, for example. The output control 98 may comprise one or more of many devices to control delivery deliver the energy or substance to the eye such as a pump, an optical shutter, an electrical switch, or a gain control, for example.

Figure 6B:
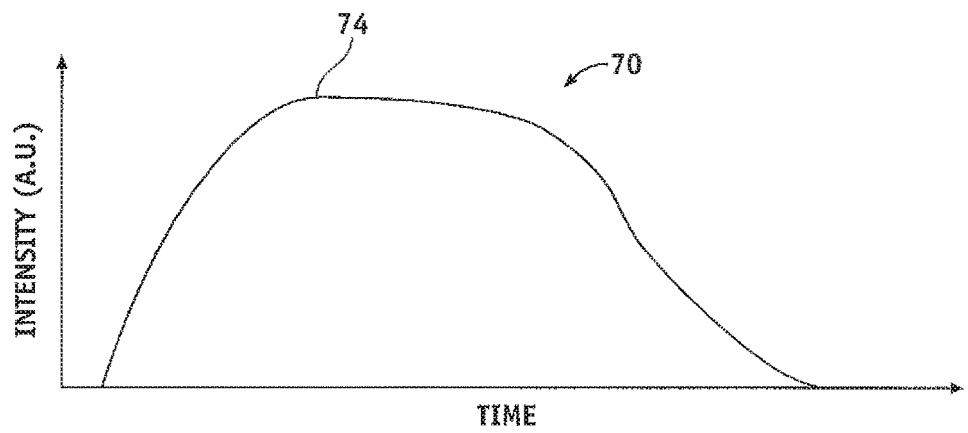
FIG. 6B shows the treatment profile to stiffen the intermediate portion of the lens capsule with the apparatus as in FIG. 6A, in accordance with embodiments of the present invention.

FIG. 6B shows the treatment profile 74 to stiffen the intermediate portion of the lens capsule with the one or more of the energy or substance 70 delivered with the apparatus 90 as in FIG. 6A. The treatment profile 74 may comprise an intensity of or amount delivered over a time period so as to stiffen the tissue of the lens capsule, for example without substantially shrinking the tissue of the lens capsule and such that the thickness of the lens capsule is substantially maintained. The tissue may be stiffened such that optical clarity of the tissue portion is substantially maintained.

Experimental and Computer Modeling

Figure 7:
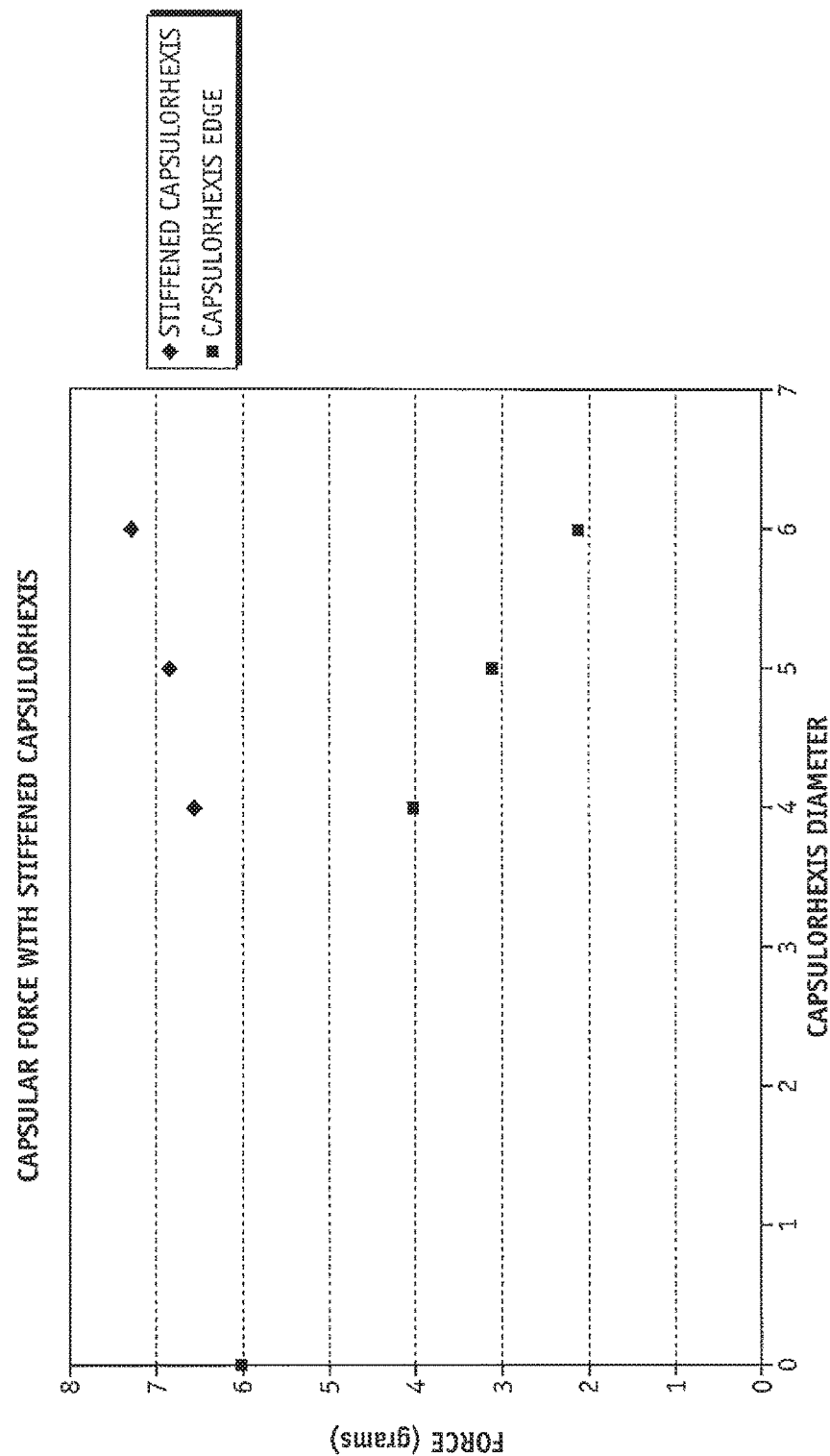
FIG. 7 shows a graph of accommodative force of the peripheral portion of the lens with stiffening of the intermediate portion based on calculations.

FIG. 7 shows a graph of radial accommodative force of the peripheral portion of the lens with stiffening of the intermediate portion based on calculations. The radial force was determined using finite element analysis and known material properties and geometries of the lens capsule. The finite element modeling used Abaqus™ software commercially available from Simulia of Providence, R.I.

The capsule was modeled with finite element shells having a uniform thickness of about 30 um. The intermediate portion of the lens capsule corresponding to the stiffened tissue was constrained such that the radial position remained fixed but was allowed to move along the axis of the coordinate system, as described herein. The radial location of the stiffened intermediate portion of lens capsule tissue was fixed at a radial distance. The lens profile in the non-stretched lens condition corresponding to accommodation was used to determine the fixed radial distance of the stiffened tissue of the intermediate portion of the lens capsule. This fixed radius condition corresponds to treatment to stiffen tissue when the eye accommodates. Alternatively, the tissue can be stiffened such that the radial distance of the intermediate portion is fixed at a radial distanced corresponding to a partially stretched lens capsule, for example. The stiffened tissue can be adjusted, for example with retreatment. Although the initial force determined with the finite element modeling was somewhat higher for the normal lens capsule, for example about 30 g, this elevated force can be related to modeling of the lens capsule with uniform thickness. Based on the teachings described herein, a person of ordinary skill in the art can model the lens capsule with varying thickness and material properties to determine the radial force for the stiffening tissue treatment.

With the non-stiffened capsulorhexis, the inward force of the lens capsule corresponding to accommodation decreased to about 4, 3 and 2 grams with capsulorhexis diameters of 4, 5 and 6 mm respectively. With the stiffened capsulorhexis having the fixed radius of the capsulorhexis edge corresponding to treatment to stiffen tissue of the intermediate portion of the lens capsule, the inward force of the lens capsule corresponding to accommodation increased to 6.5, 6.8 and 7.2 grams, with capsulorhexis diameters of 4, 5 and 6 mm respectively.

The unexpected results of these calculations indicate that stiffening of the intermediate portion as described herein can increase accommodative force following capsulorhexis as compared to non-stiffened capsulorhexis. These calculations also indicate that stiffening of the intermediate portion of the normal lens capsule can increase redistribute forces of the lens capsule so as to increase the amount of accommodation of the natural lens.

Experiments can be performed to determine the profile of the one or more of the energy or substance so as to stiffen the intermediate portion of the lens capsule, for example without shrinking the intermediate portion of the lens capsule and such that the thickness of the stiffened tissue is substantially maintained to within about +/−30%, for example to within 20%, of the pre-treatment thickness. For example, tissue can be heated to a temperature for a period of time corresponding to a temperature below the cauterizing temperature that can shrink tissue. In many embodiments, tissue can be heated so as to stiffen, for example so as to coagulate or denature collagen below the cauterizing temperature. For example, egg white can provide an in vitro model for thermal heating suitable to stiffen tissue.

Lens capsules can be treated with the one or more of the agent or energy as described herein. The capsules can be extracted, and the modulus of the lens capsule can be measured after stiffening treatment, for example.

Following in vitro measurements, in vivo measurement can be performed on living eyes. The change in refraction and accommodation can be measured so as to ensure that the amount of accommodation increases by at least about 1D for at least about 3 months in a primate animal model and the refraction can be measured so as to ensure that the refraction changes by no more than about 2 D, for example no more than about 1D with at least 1D of increased accommodation.

Clinical trials can be performed to determine the amount of accommodation increased with the tissue stiffening as described herein.

Based on the teachings described herein a person of ordinary skill in the art can determine the treatment profile 70 so as to treat tissue to stiffen the tissue of the intermediate portion of the capsule, for example to stiffen without substantial shrinkage and in at least some embodiments such that the stiffened lenses capsule remains optically clear.

While the exemplary embodiments have been described in some detail, by way of example and for clarity of understanding, those of skill in the art will recognize that a variety of modifications, adaptations and changes may be employed. Hence the scope of the present invention shall be limited solely by the claims.

What is claimed is:

1. An apparatus to treat an eye, the eye having a lens comprising a capsule, the apparatus comprising:
    a delivery device configured to be coupled to an intermediate portion of the capsule to deliver one or more of an energy or a substance to the intermediate portion of the capsule to stiffen the intermediate portion of the capsule; and
    circuitry coupled to the delivery device to deliver the one or more of the energy or the substance to the eye to stiffen the intermediate portion of the capsule.

2. The apparatus of claim 1, wherein the energy is selected from the group consisting of laser energy, mechanical energy, electromagnetic energy, RF energy, microwave energy, light energy, UV light energy, visible light energy or infrared light energy.

3. The apparatus of claim 2, wherein the delivery device is comprised of a probe with a probe tip at a distal end of the probe and wherein the energy is emitted by the probe tip.

4. The apparatus of claim 2, wherein the energy stiffens the intermediate portion to increase curvature or movement anteriorly of at least a portion of the lens when the eye accommodates.

5. The apparatus of claim 4, wherein the intermediate portion is stiffened such that far vision of the eye is maintained to within about 1 D and the amount of accommodation of the eye is increased by at least 1 D.

6. The apparatus of claim 1, wherein the substance is selected from the group
    consisting of an adhesive, a tissue fixative, riboflavin, a crosslinker, or a substance to inhibit nutrients to the intermediate portion.

7. The apparatus of claim 6, wherein the delivery device is comprised of a probe with a probe tip at a distal end of the probe and wherein the energy is emitted by the probe tip.

8. The apparatus of claim 6, wherein the substance stiffens the intermediate portion to increase curvature or movement anteriorly of at least a portion of the lens when the eye accommodates.

9. The apparatus of claim 8, wherein the intermediate portion is stiffened such that far vision of the eye is maintained to within about 1 D and the amount of accommodation of the eye is increased by at least 1 D.

* * * * *